US008293746B2

(12) United States Patent
Bold et al.

(10) Patent No.: US 8,293,746 B2
(45) Date of Patent: Oct. 23, 2012

(54) PYRIMIDINYL ARYL UREA DERIVATIVES BEING FGF INHIBITORS

(75) Inventors: Guido Bold, Gipf-Oberfrick (CH); Pascal Furet, Thann (FR); Vito Guagnano, Basel (CH)

(73) Assignee: Novartis AG, Basel (CH)

( * ) Notice: Subject to any disclaimer, the term of this patent is extended or adjusted under 35 U.S.C. 154(b) by 595 days.

(21) Appl. No.: 12/158,873

(22) PCT Filed: Dec. 20, 2006

(86) PCT No.: PCT/EP2006/070046
§ 371 (c)(1),
(2), (4) Date: Jun. 23, 2008

(87) PCT Pub. No.: WO2007/071752
PCT Pub. Date: Jun. 28, 2007

(65) Prior Publication Data
US 2008/0312248 A1 Dec. 18, 2008

Related U.S. Application Data

(60) Provisional application No. 60/752,711, filed on Dec. 21, 2005.

(51) Int. Cl.
*C07D 403/12* (2006.01)
*A61K 31/505* (2006.01)
(52) U.S. Cl. .................. 514/252.14; 544/295
(58) Field of Classification Search .................. 544/122, 544/295, 326; 514/235.8, 252.14, 256
See application file for complete search history.

(56) References Cited

U.S. PATENT DOCUMENTS

| 3,759,921 A | 9/1973 | Paget et al. |
| 2003/0069284 A1 | 4/2003 | Keegan et al. |
| 2004/0014765 A1 | 1/2004 | Boyle et al. |
| 2004/0034038 A1 | 2/2004 | Li et al. |
| 2004/0116388 A1 | 6/2004 | Armistead et al. |
| 2010/0120773 A1 | 5/2010 | Guagnano et al. |

FOREIGN PATENT DOCUMENTS

| WO | 01/25220 A1 | 4/2001 |
| WO | WO01/25220 A1 | 4/2001 |
| WO | 02/070494 A1 | 9/2002 |
| WO | 03/099771 A2 | 12/2003 |
| WO | 03/101444 A1 | 12/2003 |
| WO | 2004/058713 A1 | 7/2004 |
| WO | 2005/030735 A1 | 4/2005 |
| WO | 2005/051366 A2 | 6/2005 |
| WO | 2005/113548 A1 | 12/2005 |
| WO | 2005/121147 A1 | 12/2005 |
| WO | WO2006/000420 A1 | 1/2006 |
| WO | 2006/053227 A2 | 5/2006 |
| WO | WO2007/024754 A1 | 3/2007 |

OTHER PUBLICATIONS

Desai et al., "Synthesis of 2-(2'-Methoxyanilino)-4(benzamido-2'-yloxy)-6-(substituted-phenylureido)-s-triazine Derivatives and Study of their Antibacterial Activity", J. Indian Chem. Soc., vol. 64, pp. 773-774, 1987.
Desai et al., "Synthesis and Antimicrobial Activity of 2-[4'-(4"-Acetamidophenyl)thiazol-2'-ylamino]-4-(4'-methoxyphenylamino)-6-(aryluredo)-s-trizine and 2-[4'-(4"-Acetamidophenyl)thiazol-2'-ylamino)-4,6-bis(arylureido)-s-triazine Derivatives", J. Indian Chem Soc., vol. 71 pp. 151-153, 1994.
Hurst et al., "The Synthesis of Some Pyrimidinyl and Thiazolyl Ureas and Thioureas and Some Related Compounds", Aust. J. Chem, vol. 41 pp. 1221-1229, 1988.
Kelarev et al., "Synthesis and Mass Spectrometric Study of Carbamide Derivatives of sym-Triazine", Chemistry of Heterocyclic Compounds, vol. 23, pp. 298-304, 1987.
Ling, et al., Selenium-catalyzed carbonylation of substituted nitrobenzenes with aminomethylpyrimidines as co-reagents to synthesize N-phenyl-N' -methylpyrimidylurea derivatives, Journal of Molecular Catalysis A: Chemical, vol. 202 pp. 23-29, 2003.
Maier et al., "Development of N-4,6-pyrimidine-N-alkyl-N'-phenyl Ureas as Orally Active Inhibitors of Lymphocyte Specific Tyrosine Kinase", Bioorganic & Medicinal Chemistry Letters, 16, pp. 3646-3650, 2006.
Modi, et al., "Synthesis of 2-(2', 4'—Dihydroxy-1'-Phenyl)-4-Morpholino-6-Arylureido-S-Triazine Derivatives", Acta Ciencia Indica, vol. XX C. No. 1, 001 pp. 1-3, 1994.
Modi et al., "Synthesis of Monochlorotriazinyl Reactive Dyes from 1-Naphthol-7-amino-3-sulphonic Acid and their Application", J. Indian Chem. Soc., vol. 71 pp. 697-700, 1994.
Overberger et al., "Monomer Synthesis. Triazines. The Reaction of Phenylbiguanide with Ethyl Oxalate and Ethyl Formate", Journal of the American Chemical Society, vol. 76, pp. 93-96, 1954.
Paget, et al., "Heterocyclic Substituted Ureas. III. Immunosuppressive and Antiviral 2-Pyrimidylureas", Journal of Medicinal Chemistry, vol. 12 No. 5 pp. 1097-1098, 1969.
Traverso et al., "The Syntheses and Pharmacological Activities of Amide, Sulfamide, and Urea Derivatives of 4,6-Diaminopynmidines", Journal of Medicinal and Pharmaceutical Chemistry, vol. 5, pp. 808-815, 1962.
Urbanski, et al., Potential Antimalarial Compounds. IX. Pyrimidine Derivatives of Urea and Guanidine, Journal of Medicinal Chemistry, vol. 10 No. 4 pp. 521-525, 1967.

*Primary Examiner* — Deepak Rao
(74) *Attorney, Agent, or Firm* — Stephen Johnson; Laura Madden

(57) ABSTRACT

The invention relates to heteroaryl aryl ureas of the formula IA,

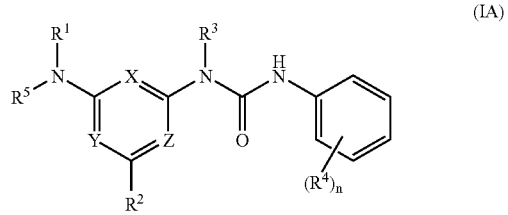

(IA)

wherein the radicals and symbols have the meanings as defined herein, the use of such compounds in the treatment of protein kinase dependent diseases; to pharmaceutical preparations comprising said heteroaryl aryl ureas, to processes for the manufacture of such novel compounds and to methods of treatment comprising the use of such heteroaryl aryl ureas.

5 Claims, No Drawings

PYRIMIDINYL ARYL UREA DERIVATIVES BEING FGF INHIBITORS

This application is a U.S. National Phase filing of International Application Serial No. PCT/EP2006/070046 filed 20 Dec. 2006, and claims priority to U.S. Provisional Application Ser. No. 60/752,711 filed 21 Dec. 2005, the contents of which are incorporated herein by reference in their entirety.

SUMMARY OF THE INVENTION

The invention relates to novel compounds, formulations, methods and uses. More particularly it relates to novel heteroaryl aryl ureas, and/or the use of or methods comprising the use of compounds, which may be described as heteroaryl aryl ureas, in the treatment, or in the manufacture of pharmaceutical formulations useful in the treatment, of protein kinase dependent diseases. The invention further relates to methods of use of such compounds in the treatment of said diseases, pharmaceutical preparations comprising heteroaryl aryl ureas, and processes for the manufacture of said novel heteroaryl aryl ureas. The invention relates to other subject matter as disclosed below.

BACKGROUND OF THE INVENTION

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive PK activity has been observed in many disease states including benign and malignant proliferative disorders. In many cases, it has been possible to treat diseases in vitro and in many cases in vivo, such as proliferative disorders, by making use of PK inhibitors.

The kinases fall largely into two groups, those specific for phosphorylating serine and threonine, and those specific for phosphorylating tyrosine. In addition, some kinases, referred to as "dual specificity" kinases, are able to phosphorylate tyrosine as well as serine/threonine residues.

Protein kinases can also be characterized by their location within the cell. Some kinases are transmembrane receptor proteins capable of binding ligands external to the cell membrane. Binding the ligands alters the receptor protein kinase's catalytic activity. Others are non-receptor proteins lacking a transmembrane domain and yet others are ecto-kinases that have a catalytic domain on the extracellular (ecto) portion of a transmembrane protein or which are secreted as soluble extracellular proteins.

Many kinases are involved in regulatory cascades where their substrates may include other kinases whose activities are regulated by their phosphorylation state. Thus, activity of a downstream effector is modulated by phosphorylation resulting from activation of the pathway.

Receptor protein tyrosine kinases (RPTKs) are a sub-class of transmembrane-spanning receptors endowed with intrinsic, ligand-stimulatable tyrosine kinase activity. RPTK activity is tightly controlled. When mutated or altered structurally, RPTKs can become potent oncoproteins, causing cellular transformation or at least deregulation. In principle, for all RPTKs involved in cancer, oncogenic deregulation results from relief or perturbation of one or several of the autocontrol mechanisms that ensure the normal repression of catalytic domains. More than half of the known RPTKs have been repeatedly found in either mutated or overexpressed forms associated with human malignancies (including sporadic cases; Blume-Jensen et al., Nature 411: 355-365 (2001)).

RPTK over-expression leads to constitutive kinase activation by increasing the concentration of dimers. Examples are Neu/ErbB2 and epidermal growth factor receptor (EGFR), which are often amplified in breast and lung carcinomas and the fibroblast growth factors (FGFR) associated with skeletal and proliferative disorders (Blume-Jensen et al., 2001).

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., Cell Growth & Differentiation, 8, 3-10 (1997). On the other hand, unwanted angiogenesis is a hallmark of several diseases, such as retinopathies, psoriasis, rheumatoid arthritis, age-related macular degeneration (AMD), and cancer (solid tumors). Folkman, Nature Med., 1, 27-31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and, as FLK-1); FGF-R (fibroblast growth factor receptor); and TEK (also known as Tie-2).

TEK (also known as Tie-2) is a receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., Science, 277, 55-60 (1997).

Administration of Ad-ExTek, a soluble adenoviral expressed extracellular domain of Tie-2, inhibited tumour metastasis when delivered at the time of surgical excision of primary tumors in a clinically relevant mouse model of tumor metastasis (Lin et al., Proc Natl Acad Sci USA 95, 8829-8834 (1998)). The inhibition of Tie-2 function by ExTek may be a consequence of sequestration of the angiopoietin ligand and/or heterodimerisation with the native Tie-2 receptor. This study demonstrates that disruption of Tie-2 signalling pathways, first, may be well tolerated in healthy organisms and, second, may provide therapeutic benefit.

The Philadelphia Chromosome is a hallmark for chronic myelogenous leukaemia (CML) and carries a hybrid gene that contains N-terminal exons of the bcr gene and the major C-terminal part (exons 2-11) of the c-abl gene. The gene product is a 210 kD protein (p210 Bcr-Abl). The Abl-part of the Bcr-Abl protein contains the abl-tyrosine kinase which is tightly regulated in the wild type c-abl, but constitutively activated in the Bcr-Abl fusion protein. This deregulated tyrosine kinase interacts with multiple cellular signaling pathways leading to transformation and deregulated proliferation of the tells (Lugo et al., Science 247, 1079 [1990]).

Mutant forms of the Bcr-Abl protein have also been identified. A detailed review of Bcr-Abl mutant forms has been published (Cowan-Jones et al, Mini Reviews in Medicinal Chemistry, 2004, 4 285-299).

EphB4 (also named HTK) and its ligand, ephrinB2 (HTKL) have critical roles in establishing and determining vascular networks. On the venous epithelium, EphB4 is expressed specifically, while, during early stages of vascular development, ephrinB2 is specifically and reciprocally expressed on arterial endothelial cells. Dysfunctional genes lead to embryonic lethality in mice, and the embryos show identical defects in forming capillary connections in case of either defect ephrinB2 and EphB4. Both are expressed at the first site of hematopoiesis and vascular development during embryogenesis. An essential role for proper hematopoietic, endothelial, hemangioblast and primitive mesoderm development was established. EphB4 deficiency results in an alteration in the mesodermal differentiation outcome of embryonic stem cells. Ectopic expression of EphB4 in mammary tissue results in disordered architecture, abnormal tissue function and a predisposition to malignancy (see e.g. N. Munarini et al., J. Cell. Sci. 115, 25-37 (2002)). From these and other data, it has been concluded that inadequate EphB4 expression may be involved in the formation of malignancies and thus that inhibition of EphB4 can be expected to be a tool to combat malignancies, e.g. cancer and the like.

c-Src (also known as p60 c-Src) is cytosolic, non-receptor tyrosine kinase. c-Src is involved in the transduction of mitogenic signals from a number of polypeptide growth factors such as epidermal growth factor (EGF) and platelet-derived growth factor (PDGF). c-Src is over-expressed in mammary cancers, pancreatic cancers, neuroblastomas, and others. Mutant c-Src has been identified in human colon cancer. c-Src phosphorylates a number of proteins that are involved in regulating cross-talk between the extracellular matrix and the cytoplasmic actin cytoskeleton. Modulation cSrc activity could have implications in diseases relating to cell proliferation, differentiation and death. See Bjorge, J. D., et. al. (2000) Oncogene 19(49):5620-5635; Halpern, M. S., et. al. (1996) Proc. Natl. Acad. Sci. U.S.A. 93(2), 824-7; Belsches, A. P., et. al. (1997) Frontiers in Bioscience [Electronic Publication] 2:D501-D518; Zhan, X., et. al (2001) Chemical Reviews 101:2477-2496; Haskell, M. D., et. al. (2001) Chemical Reviews 101:2425-2440.

The fms-like tyrosine kinase 3 (FLT3) receptor tyrosine kinase is now recognized to be a critical mediator in the pathogenesis of myeloid and some lymphoid leukemias. Activation of FLT3 on leukemic cells by FLT3 ligand leads to receptor dimerization and signal transduction in pathways that promote cell growth and inhibit apoptosis (Blood, Vol. 98, No. 3, pp. 885-887 (2001)).

Use of tyrosine kinase inhibitors for AML therapy is hindered by the acquisition of mutations in the kinase catalytic domain, and in the case of BCR-ABL, these mutations confer resistance to imatinib.

FLT3 is widely expressed in AML and some cases of acute lymphocytic leukemia. Activating mutations in FLT3 confer a poor risk in patients with AML. Thus, FLT3 is a promising target for therapeutic intervention.

Platelet-derived growth factor receptor (PDGFR) tyrosine kinase is expressed in a number of tumours such as small-cell lung cancer, prostate cancer, and glioblastoma as well as in the stromal and vascular compartments of many tumors. Expression of both PDGF and PDGF receptors (PDGFRs) has been observed in pancreatic cancer (Ebert Met al., Int J Cancer, 62:529-535 (1995).

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) Cell 74:215). The Raf serine/threonine kinases are considered to be the primary Ras effectors involved in the proliferation of animal cells (Avruch et al. (1994) Trends Biochem. Sci. 19:279).

Raf kinase has three distinct isoforms, Raf-1 (c-Raf, A-Raf, and B-Raf, distinguished by their ability to interact with Ras, to activate MAPK kinase pathway, tissue distribution and sub-cellular localization (Marias et al., Biochem. J. 351: 289-305, 2000; Weber et. al., Oncogene 19:169-176, 2000; Pritchard et al., Mol. Cell. Biol. 15:6430-6442, 1995).

Recent studies have shown that B-Raf mutation in the skin nevi is a critical step in the initiation of melanocytic neoplasia (Pollock et. al., Nature Genetics 25: 1-21 2002). Furthermore, most recent studies have emerged that activating mutation in the kinase domain of B-Raf occurs in about 66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harborring activating mutations of Raf itself. In early clinical trails an inhibitor of Raf-1 kinase, that also inhibits B-Raf, has shown promise as a therapeutic agent in cancer therapy (Crump, Current Pharmaceutical Design 8: 2243-2248, 2002; Sebastien et. al., Current Pharmaceutical Design 8: 2249-2253, 2002).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996).

Fibroblast Growth Factors

Normal growth, as well as tissue repair and remodeling, require specific and delicate control of activating growth factors and their receptors. Fibroblast Growth Factors (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz, Novartis Found Svmp 232: 63-76; discussion 76-80, 272-82 (2001)).

The biological action of FGFs is mediated by specific cell surface receptors belonging to the RPTK family of protein-kinases. These proteins consist of an extracellular ligand binding domain, a single transmembrane domain and an intracellular tyrosine kinase domain which undergoes phosphorylation upon binding of FGF. Four FGFRs have been identified to date: FGFR1 (also called Flg, fms-like gene, fit-2, bFGFR, N-bFGFR or Cek1), FGFR2 (also called Bek-Bacterial Expressed Kinase-, KGFR, Ksam, Ksaml and Cek3), FGFR3 (also called Cek2) and FGFR4. All mature FGFRs share a common structure consisting of an amino terminal signal peptide, three extracellular immunoglobulin-like domains (Ig domain I, Ig domain II, Ig domain III), with an acidic region between Ig domains (the "acidic box" domain), a trans-membrane domain, and intracellular kinase domains (Ullrich and Schiessinger, Cell 61: 203, 1990; Johnson and Williams (1992) Adv. Cancer Res. 60:1-41). The distinct FGFR isoforms have different binding affinities for the different FGF ligands, thus FGF8 (androgen-induced growth factor) and FGF9 (glial activating factor) appear to have increased selectivity for FGFR3 (Chellaiah et al. J. Biol. Chem. 1994; 269: 11620).

Another major class of cell surface binding sites includes binding sites for heparan sulfate-proteoglycans (HSPG) that are required for high affinity interaction and activation of all members of the FGF family. Tissue-specific expression of heparan sulfate structural variants confer ligand-receptor specificity and activity of FGFs FGFR-Related Diseases Recent discoveries show that a growing number of skeletal abnormalities, including achondroplasia, the most common form of human dwarfism, result from mutations in FGFRs.

Specific point mutations in different domains of FGF-R1, FGF-R2 and FGFR3 are associated with autosomal dominant human skeletal dysplasias classified as craniosyneostosis syndromes and dwarfism syndromes (Coumoul and Deng, Birth Defects Research 69: 286-304 (2003). FGF-R3 mutations-associated skeletal dysplasias include hypochondroplasia, severe achondroplasia with developmental delay and acanthosis nigricans (SADDAN) and thanatophoric dysplasia (TD) (Webster et al., Trends Genetics 13 (5): 178-182 (1997); Tavormina et al., Am. J. Hum. Genet., 64: 722-731 (1999)). FGFR3 mutations have also been described in two craniosynostosis phenotypes: Muenke coronal craniosynostosis (Bellus et al., Nature Genetics, 14: 174-176 (1996); Muenke et al., Am. J. Hum. Genet., 60: 555-564 (1997)) and Crouzon syndrome with acanthosis nigricans (Meyers et al., Nature Genetics, 11: 462-464 (1995)). Crouzon syndrome is associated with specific point mutations in FGFR2 and both familial and sporadic forms of Pfeiffer syndrome are associated with mutations in FGFR1 and FGFR2 (Galvin et al., PNAS USA, 93: 7894-7899 (1996); Schell et al., Hum Mol Gen, 4: 323-328 (1995)). Mutations in FGFRs result in constitutive activation of the mutated receptors and increased receptor protein tyrosine kinase activity, rendering cells and tissue unable to differentiate.

Specifically, the achondroplasia mutation results in enhanced stability of the mutated recaptor, dissociating receptor activation from down-regulation, leading to restrained chondrocyte maturation and bone growth inhibition (reviewed in Vajo et al., Endocrine Reviews, 21 (1): 23-39 (2000)).

There is accumulating evidence for mutations activating FGFR3 in various types of cancer.

Constitutively activated FGFR3 in two common epithelial cancers, bladder and cervix, as well as in multiple myeloma, is the first evidence of an oncogenic role for FGFR3 in carcinomas. In addition, a very recent study reports the presence of FGFR3 activating mutations in a large proportion of benign skin tumors (Logie et al., Hum Mot Genet. 2005). FGFR3 currently appears to be the most frequently mutated oncogene in bladder cancer where it is mutated in almost 50% of the total bladder cancer cases and in about 70% of cases having superficial bladder tumors (Cappellen, et al., Nature Genetics 1999, 23; 19-20; van Rhijn, et al., Cancer Research 2001, 61: 1265-1268; Billerey, et al, Am. J. Pathol. 2001, 158:1955-1959, WO 2004/085676). Also, overexpression of FGFR3 has been reported in bladder cancer (superficial and invasive) (Gomez-Roman et al. Clinical Cancer Research 2005).

FGFR3 aberrant overexpression as a consequence of the chromosomal translocation t(4,14) is reported in 10-25% of multiple myeloma cases (Chesi et al., Nature Genetics 1997, 16: 260-264; Richelda et al., Blood 1997, 90:4061-4070; Sibley et al., BJH 2002, 118: 514-520; Santra et al., Blood 2003, 101: 2374-2476). FGFR3 activating mutations are seen in 5-10% of multiple myelomas with t(4,14) and are associated with tumor progression (Chesi et al., Nature Genetics 1997, 16: 260-264; Chesi et al., Blood, 97 (3): 729-736 (2001); Intini, et al, BJH 2001, 114: 362-364).

In this context, the consequences of FGFR3 signaling often appear to be cell type-specific. In chondrocytes, FGFR3 hyperactivation results in growth inhibition (reviewed in Omitz, 2001), whereas in the myeloma cell it contributes to tumor progression (Chesi et al., 2001).

The inhibition of FGFR3 activity has been found to represent a means for treating T cell mediated inflammatory or autoimmune diseases, as for example in treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis. See WO 2004/110487.

Disorders resulting from FGFR3 mutations are described also in WO 03/023004 and WO 02/102972.

Among the diseases promoted by FGFR3 and also other FGFRs (especially in connection with e.g. aberrant FGF23 serum levels), further Autosomal Dominant Hypophosphatemic Rickets (ADHR), X-chromosome linked hypophosphatemic rickets (XLH), tumor-induced Osteomalacia (TIO), fibrous dysplasia of the bone (FH) are to be mentioned (see also X. Yu et al., Cytokine & Growth Factor Reviews 16, 221-232 (2005), and X. Yu et al., Therapeutic Apheresis and Dialysis 9(4), 308-312 (2005)).

Gene amplification and/or overexpression of FGFR1, FGFR2 and FGFR4 have been implicated in breast cancer (Penault-Llorca et al., Int J Cancer 1995; Theillet et al., Genes Chrom. Cancer 1993; Adnane et al., Oncogene 1991; Jaakola et al., Int J Cancer 1993; Yamada et al., Neuro Res 2002). Overexpression of FGFR1 and FGFR4 is also associated with pancreatic adenocarcinomas and astrocytomas (Kobrin et al., Cancer Research 1993; Yamanaka et al., Cancer Research 1993; Shah et al., Oncogene 2002; Yamaguchi et al., PNAS 1994; Yamada et al., Neuro Res 2002). Prostate cancer has also been related to FGFR1 overexpression (Giri et al., Clin Cancer Res 1999).

FGFs/FGFRs are also involved in angiogenesis. Therefore, targeting the FGFR system is also foreseen as an anti-angiogenic therapy to treat primary tumors, as well as metastasis. (see e.g. Presta et al., Cytokine & Growth Factors Reviews 16, 159-178 (2005)).

Mutations, especially in FGFR3 (e.g. FGFR3b) have also been described to be responsible for constitutive activation of these receptors in the case of oral squameous cell carcinoma (see e.g. Y. Zhang et al, Int. J. Cancer 117, 166-168 (2005).

Enhanced (especially bronchial) expression of FGFRs, especially FGFR1, has been reported to be associated with Chronic Obstructive Pulmonary Disease (COPD) (see e.g. A. Kranenburg et al., J. Pathol. 206, 28-38 (2005)).

Chromosomal translocations involving the FGF-R1 locus and resulting in activated forms of FGR-R1 have been reported to be responsible for 8p11 myeloproliferative syndrome=Eosinophilic Myeloproliferative Syndrome (EMS) (see D. Macdonald et al., Cross NCP (2002) Acta Haematologica 107: 101-107).

Methods of antagonizing FGFRs, especially FGFR1 or FGFR4, have also been described to be useful in the treatment of obesity, diabetes and/or diseases related thereto, such as metabolic syndrome, cardiovascular diseases, hypertension, aberrant cholesterol and triglyceride levels, dermatological disorders (e.g. infections, varicose veins, Acanthosis nigricans, eczema, exercise intolerance, diabetes type 2, insulin resistance, hypercholesterolemia, cholelithiasis, orthopedic injury, thromboembolic disease, coronary or vascular restriction (e.g. atherosclerosis), daytime sleepiness, sleep apnoea, end stage renal disease, gallbladder disease, gout, heat disorders, impaired immune response, impaired respiratory function, infections following wounds, infertility, liver disease, lower back pain, obstetric and gynecological complications, pancreatitis, stroke, surgical complications, urinary stress incontinence and/or gastrointestinal disorders (see e.g. WO 2005/037235 A2).

Acidic Fibroblast Growth Factor (especially FGF-1) and FGFR1 have also been described to be involved in aberrant signaling in retinoblastoma, leading to proliferation upon binding of FGF-1 (see e.g. S. Siffroi-Fernandez et al., Arch. Opthalmology 123, 368-376 (2005)).

The growth of synovial sarcomas has been shown to be inhibited by disruption of the Fibroblast Growth Factor Signaling Pathway (see e.g. T. Ishibe et al., Clin. Cancer Res. 11(7), 2702-2712 (2005)).

Further, FGFR involvement in the case of thyroid carcinoma could be demonstrated.

Epidermal Growth Factor Family and Related Diseases

The epidermal growth factor receptor (EGF-R) and ErbB-2 kinase are protein tyrosine kinase receptors which, together with their family members ErbB-3 and ErbB-4, play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase is a prerequisite for cell division and hence for the proliferation of the cell population. Most importantly, overexpression of the EGF-R (HER-1) and/or ErbB-2 (HER-2) has been observed in substantial fractions of many human tumours. EGF-R, e.g., was found to be overexpressed in non small-cell lung cancers, squameous carcinoma (head and neck), breast, gastric, ovarian, colon and prostate cancers as well as in gliomas. ErbB-2 was found to be overexpressed in squameous carcinoma (head and neck), breast, gastric, and ovarian cancers as well as in gliomas.

In all the cases mentioned above where protein kinases are involved the modulation of an aberrant activity (especially the inhibition of an activity of such a kinase) can be expected reasonably to be useful in the diseases mentioned.

There is thus an unmet need for highly affine and/or selective molecules capable of blocking aberrant constitutive receptor protein tyrosine kinase activity, in particular FGFR activity, thereby addressing the clinical manifestations associated with the above-mentioned mutations, and modulating various biological functions.

In view of the large number of protein kinase inhibitors and the multitude of proliferative and other PK-related diseases, there is an ever-existing need to provide novel classes of compounds that are useful as PK inhibitors and thus in the treatment of these Protein Tyrosine Kinase (PTK) related diseases. What is required are new classes of pharmaceutically advantageous PK inhibiting compounds.

GENERAL DESCRIPTION OF THE INVENTION

It has now been found that the compounds given in more detail below, which may be described as belonging to the heteroaryl aryl urea class, show inhibition of a number of protein tyrosine kinases, especially any such kinase mentioned herein, more especially of FGFR.

As examples of kinases inhibited by the compounds of the disclosure there may be mentioned especially FGFR1, FGFR2, FGFR3 and FGFR4. Another inhibited kinase is the recaptor tyrosine kinase VEGF-R, in particular the VEGF receptor KDR (VEGF-R2). The disclosed compounds are appropriate for the inhibition of one or more of these and/or other protein tyrosine kinases and/or for the inhibition of mutants of these enzymes. In view of these activities, the compounds can be used for the treatment of diseases related to, especially, aberrant or excessive activity of such types of kinases, especially those mentioned.

The compounds of the disclosure can exist in different forms, such as free acids, free bases, ester and other prodrugs, salts and tautomers, for example, and the disclosure includes all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount. Included in the scope of protection therefore are packages which include a description or instructions which indicate that the package contains a species or pharmaceutical formulation or composition of the invention and a product which is or comprises, or purports to be or comprise, such a formulation, composition or species.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Further aspects and embodiments of the disclosure are set forth in the following description and claims.

DETAILED DESCRIPTION OF THE INVENTION

It has now been found that the novel compounds of the formula IA,

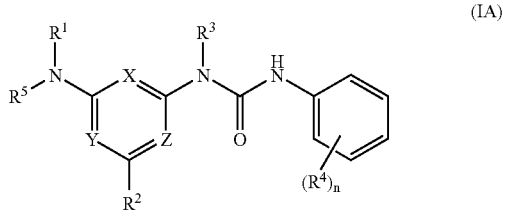

wherein
two of X, Y and Z are N (nitrogen), the third is CH or N (preferably Y and Z are N and Z is CH); and
wherein either
$R^1$ is phenyl that is substituted by hydroxy, phenyl-$C_1$-$C_7$-alkyloxy, piperazin-1-yl or 4-(phenyl-$C_1$-$C_7$-alkyl)-piperazin-1-yl; or phenyl that is substituted by (i) halo or $C_1$-$C_7$-alkoxy and in addition (ii) by hydroxy, phenyl-$C_1$-$C_7$-alkyloxy, N-mono- or N,N-di-($C_1$-$C_7$-alkyl)-amino-$C_1$-$C_7$-alkyl, pyrrolidino-$C_1$-$C_7$-alkoxy, 1-($C_1$-$C_7$-alkyl)-piperidin-4-yl, morpholino-$C_1$-$C_7$-alkoxy, thiomorpholino-$C_1$-$C_7$-alkoxy, piperazin-1-yl, 4-(phenyl-$C_1$-$C_7$-alkyl)-piperazin-1-yl, 4-($C_1$-$C_7$-alkyl)-piperazin-1-yl, [4-($C_1$-$C_7$-alkyl)-piperazin-1-yl]-$C_1$-$C_7$-alkyl, N-mono- or N,N-di-($C_1$-$C_7$-alkyl)-amino-$C_1$-$C_7$-alkyl, N-mono- or N,N-di-($C_1$-$C_7$-alkyl)-amino-$C_1$-$C_7$-alkoxy, [4-($C_1$-$C_7$-alkyl)-piperazin-1-yl]-$C_1$-$C_7$-alkoxy, [4-($C_1$-$C_7$-alkyl)-piperazin-1-yl]-carbonyl;
$R^2$ is hydrogen, $C_1$-$C_7$-alkyl, $C_1$-$C_7$-alkoxy or halo;
$R^3$ is hydrogen, $C_1$-$C_7$-alkyl or phenyl-$C_1$-$C_7$-alkyl,
each $R^4$ is, independently of the others, $C_1$-$C_7$-alkyl, halo-$C_1$-$C_7$-alkyl, halo or $C_1$-$C_7$-alkoxy,
and n is 0, 1, 2, 3, 4 or 5;
or
$R^1$ is phenyl that is substituted by hydroxy, phenyl-$C_1$-$C_7$-alkyloxy, piperazin-1-yl, 4-(phenyl-$C_1$-$C_7$-alkyl)-piperazin-1-yl; N-mono- or N,N-di-($C_1$-$C_7$-alkyl)-amino-$C_1$-$C_7$-alkyl, pyrrolidino-$C_1$-$C_7$-alkoxy, 1-($C_1$-$C_7$-alkyl)-piperidin-4-yl, morpholino-$C_1$-$C_7$-alkoxy, thiomorpholino-$C_1$-$C_7$-alkoxy, 4-($C_1$-$C_7$-alkyl)-piperazin-1-yl, [4-($C_1$-$C_7$-alkyl)-piperazin-1-yl]-$C_1$-$C_7$-alkyl, N-mono- or N,N-di-($C_1$-$C_7$-alkyl)-amino-$C_1$-$C_7$-alkyl, N-mono- or N,N-di-($C_1$-$C_7$-alkyl)-amino-$C_1$-$C_7$-alkoxy, [4-($C_1$-$C_7$-alkyl)-piperazin-1-yl]-$C_1$-$C_7$-alkoxy, [4-($C_1$-$C_7$-alkyl)-piperazin-1-yl]-carbonyl; or phenyl that carries one of the substitutents mentioned so far in the present paragraph and in addition a substituent selected from halo and $C_1$-$C_7$-alkoxy;
$R^2$ is hydrogen, $C_1$-$C_7$-alkyl, $C_1$-$C_7$-alkoxy or halo;
$R^3$ is hydrogen, $C_1$-$C_7$-alkyl or phenyl-$C_1$-$C_7$-alkyl,
$R^5$ is hydrogen (preferred), $C_1$-$C_7$-alkyl or phenyl-$C_1$-$C_7$-alkyl,
and
either n is 3, 4 or 5 and $R^4$ is selected from $C_1$-$C_7$-alkyl, $C_1$-$C_7$-alkoxy and halo, with the proviso that at least one of each of $C_1$-$C_7$-alkyl, $C_1$-$C_7$-alkoxy and halo is present;
or n is 2 and one $R^4$ is halo-$C_1$-$C_7$-alkyl, the other $R^4$ is $C_1$-$C_7$-alkoxy;
or n is 3, 4 or 5 and $R^4$ is selected from halo, iodo and $C_1$-$C_7$-alkoxy, with the proviso that at least one of each of halo, iodo and $C_1$-$C_7$-alkoxy, is present;
or n is 3, 4 or 5 and $R^4$ I selected from halo, halo-$C_1$-$C_7$-alkyl and $C_1$-$C_7$-alkoxy, with the proviso that at least one of each of halo, halo-$C_1$-$C_7$-alkyl and $C_1$-$C_7$-alkoxy is present;
or
Y and Z are N (nitrogen) and X is CH,
wherein either
$R^1$ is 3-pyridyl which is monosubstituted by N—$C_1$-$C_7$-alkyl-piperazin-1-yl,
$R^2$ is hydrogen,
$R^3$ is hydrogen,
each $R^4$ is, independently of the others, $C_1$-$C_7$-alkyl, halo-$C_1$-$C_7$-alkyl, halo or $C_1$-$C_7$-alkoxy,
$R^5$ is hydrogen
and n is 1, 2, 3, 4 or 5;
or
a compound of the formula IA wherein $R^1$ is 4-(2-morpholin-4-yl-ethoxy)-phenylamino, $R^2$ is hydrogen, $R^3$ is hydrogen, $R^4$ is 2- and 6-chloro and 3- and 5-methoxy, n is 4, $R^5$ is hydrogen, Y and Z are N and X is CH;
or
a compound of the formula IA wherein $R^1$ is 3-(4-methyl-piperazin-1-ylmethyl)-phenylamino, $R^2$ is hydrogen, $R^3$ is methyl, $R^4$ is 2- and 6-chloro and 3- and 5-methoxy, n is 4, $R^5$ is hydrogen, Y and Z are N and X is CH,
or
a compound of the formula IA wherein $R^1$ is 3-(4-ethyl-piperazin-1-yl)-phenylamino, $R^2$ is hydrogen, $R^3$ is methyl, $R^4$ is 2- and 6-chloro and 3- and 5-methoxy, n is 4, $R^5$ is hydrogen, Y and Z are N and X is CH,
or
a compound of the formula IA wherein $R^1$ is 4-(2-morpholin-4-yl-ethoxy)-phenylamino, $R^2$ is hydrogen, $R^3$ is methyl, $R^4$ is 2- and 6-chloro and 3- and 5-methoxy, n is 4, $R^5$ is hydrogen, Y and Z are N and X is CH,
or
a compound of the formula IA wherein $R^1$ is 4-(1-ethyl-piperidin-4-yl)-phenylamino, $R^2$ is hydrogen, $R^3$ is methyl, $R^4$ is 2- and 6-chloro and 3- and 5-methoxy, n is 4, $R^5$ is hydrogen, Y and Z are N and X is CH,
or
a compound of the formula IA wherein $R^1$ is 4-(4-ethyl-piperazin-1-yl)-phenylamino, $R^2$ is hydrogen, $R^3$ is ethyl, $R^4$ is 2- and 6-chloro and 3- and 5-methoxy, n is 4, $R^5$ is hydrogen, Y and Z are N and X is CH, and/or
or
a compound of the formula IA wherein $R^1$ is 4-(4-ethyl-piperazine-1-carbonyl)-phenylamino, $R^2$ is hydrogen, $R^3$ is methyl, $R^4$ is 2- and 6-chloro and 3- and 5-methoxy, n is 4, $R^5$ is hydrogen, Y and Z are N and X is CH;
or mixtures of two or more compounds of the formula IA;
or in each case of a compound of the formula IA (as mentioned above or below) salts, prodrugs, N-oxides or esters thereof,
are useful in the treatment of disorders related to protein kinase activity, especially with regard to diseases that can be treated by Protein Tyrosine Kinase modulating compounds, more especially FGFR modulating compounds.

Therefore, the invention relates to one or more of these compounds of the formula IA, salts, prodrugs, N-oxides or esters thereof, as well as to the uses, methods and pharmaceutical formulations mentioned above.

In particular, the present inventions relates to compounds of formula IA, wherein two of X, Y and Z are N (nitrogen), the third is CH or N (preferably Y and Z are N and Z is CH); and either (A) $R^1$ is phenyl that is substituted by hydroxy, by phenyl-$C_1$-$C_7$-alkyloxy (especially benzyloxy), by piperazin-1-yl or by 4-(phenyl-$C_1$-$C_7$-alkyl)-piperazin-1-yl (especially 4-benzylpiperazin-1-yl); or phenyl that is substituted (i) (once) by halo (especially fluoro or chloro) or $C_1$-$C_7$-alkoxy (especially methoxy) and in addition (ii) (once) by hydroxy, phenyl-$C_1$-$C_7$-alkyloxy (especially benzyloxy), N-mono- or N,N-di-($C_1$-$C_7$-alkyl)-amino-$C_1$-$C_7$-alkyl (especially dimethylaminomethyl), pyrrolidino-$C_1$-$C_7$-alkoxy (especially 2-pyrrolidino-ethoxy), 1-($C_1$-$C_7$-alkyl)-piperidin-4-yl (especially 1-ethyl-piperidin 74-yl), morpholino-$C_1$-$C_7$-alkoxy (especially 2-morpholino-ethoxy), thiomorpholino-$C_1$-$C_7$-alkoxy (especially 2-thiomorpholino-ethoxy), piperazin-1-yl, 4-(phenyl-$C_1$-$C_7$-alkyl)-piperazin-1-yl (especially 4-benzylpiperazin-1-I), 4-($C_1$-$C_7$-alkyl)-piperazin-1-yl (especially 4-(methyl, ethyl or isopropyl)-piperazin-1-yl), [4-($C_1$-$C_7$-alkyl)-piperazin-1-yl]-$C_1$-$C_7$-alkyl (especially 2-[4-(methyl or ethyl)-piperazin-1-yl]-ethyl), N-mono- or N,N-di-($C_1$-$C_7$-alkyl)-amino-$C_1$-$C_7$-alkyl (especially dimethylaminomethyl), N-mono- or N,N-di-($C_1$-$C_7$-alkyl)-amino-$C_1$-$C_7$-alkoxy (especially 2-(dimethylamino)-ethoxy), [4-($C_1$-$C_7$-alkyl)-piperazin-1-yl]-$C_1$-$C_7$-alkoxy (especially 2-(4-methylpiperazin-1-yl)-ethoxy) or [4-($C_1$-$C_7$-alkyl)-piperazin-1-yl]-carbonyl (especially 4-ethylpiperazin-1-carbonyl);

$R^2$ is hydrogen (preferred), $C_1$-$C_7$-alkyl, $C_1$-$C_7$-alkoxy or (with lower preference) halo;

$R^3$ is hydrogen (preferred), $C_1$-$C_7$-alkyl (preferred) or phenyl-$C_1$-$C_7$-alkyl, each $R^4$ is, independently of the others, $C_1$-$C_7$-alkyl, halo-$C_1$-$C_7$-alkyl, halo or $C_1$-$C_7$-alkoxy, $R^5$ is hydrogen (preferred), $C_1$-$C_7$-alkyl or phenyl-$C_1$-$C_7$-alkyl, and n is 0, 1, 2, 3, 4 or 5;

or (B) wherein $R^1$ is phenyl that is substituted by hydroxy, phenyl-$C_1$-$C_7$-alkyloxy (especially benzyloxy), piperazin-1-yl, 4-(phenyl-$C_1$-$C_7$-alkyl)-piperazin-1-yl (especially 4-benzylpiperazin-1-yl), N-mono- or N,N-di-($C_1$-$C_7$-alkyl)-amino-$C_1$-$C_7$-alkyl (especially dimethylaminomethyl), pyrrolidino-$C_1$-$C_7$-alkoxy (especially 2-pyrrolidino-ethoxy), 1-($C_1$-$C_7$-alkyl)-piperidin-4-yl (especially 1-ethyl-piperidin-4-yl), morpholino-$C_1$-$C_7$-alkoxy (especially 2-morpholino-ethoxy), thiomorpholino-$C_1$-$C_7$-alkoxy (especially 2-thiomorpholino-ethoxy), 4-($C_1$-$C_7$-alkyl)-piperazin-1-yl (especially 4-(methyl, ethyl or isopropyl)-piperazin-1-yl), [4-($C_1$-$C_7$-alkyl)-piperazin-1-yl]-$C_1$-$C_7$-alkyl (especially 2-[4-(methyl or ethyl)-piperazin-1-yl]-ethyl), N-mono- or N,N-di-($C_1$-$C_7$-alkyl)-amino-$C_1$-$C_7$-alkyl (especially dimethylaminomethyl), N-mono- or N,N-di-($C_1$-$C_7$-alkyl)-amino-$C_1$-$C_7$-alkoxy (especially 2-(dimethylamino)-ethoxy), [4-($C_1$-$C_7$-alkyl)-piperazin-1-yl]-$C_1$-$C_7$-alkoxy (especially 2-(4-methylpiperazin-1-yl)-ethoxy) or [4-($C_1$-$C_7$-alkyl)-piperazin-1-yl]-carbonyl (especially 4-ethylpiperazin-1-carbonyl); or phenyl that carries one of the substitutents mentioned so far for $R^1$ in the present paragraph and in addition a substituent selected from halo and $C_1$-$C_7$-alkoxy;

$R^2$ is hydrogen (preferred), $C_1$-$C_7$-alkyl, $C_1$-$C_7$-alkoxy or (with lower preference) halo;

$R^3$ is hydrogen (preferred), $C_1$-$C_7$-alkyl (preferred) or phenyl-$C_1$-$C_7$-alkyl, $R^5$ is hydrogen (preferred), $C_1$-$C_7$-alkyl or phenyl-$C_1$-$C_7$-alkyl, and either n is 3, 4 or 5 and $R^4$ is selected from $C_1$-$C_7$-alkyl, $C_1$-$C_7$-alkoxy and halo, with the proviso that at least one of each of $C_1$-$C_7$-alkyl, $C_1$-$C_7$-alkoxy and halo is present;

or n is 2 and one $R^4$ is halo-$C_1$-$C_7$-alkyl, the other $R^4$ is $C_1$-$C_7$-alkoxy;

or n is 3, 4 or 5 and $R^4$ is selected from halo, iodo and $C_1$-$C_7$-alkoxy, with the proviso that at least one of each of halo, iodo and $C_1$-$C_7$-alkoxy, is present;

or n is 3, 4 or 5 and $R^4$ I selected from halo, halo-$C_1$-$C_7$-alkyl and $C_1$-$C_7$-alkoxy, with the proviso that at least one of each of halo, halo-$C_1$-$C_7$-alkyl and $C_1$-$C_7$-alkoxy is present;

(C) or a compound of the formula IA with the names 1-(2,6-dichloro-3,5-dimethoxy-phenyl)-3-{6-[4-(2-morpholin-4-yl-ethoxy)-phenylamino]-pyrimidin-4-yl}-urea (where, referring to formula IA, $R^1$ is 4-(2-morpholin-4-yl-ethoxy)-phenylamino, $R^2$ is hydrogen, $R^3$ is hydrogen, $R^4$ is 2- and 6-chloro and 3- and 5-methoxy and n is 4 and $R^5$ is hydrogen), 3-(2,6-dichloro-3,5-dimethoxy-phenyl)-1-methyl-1-(6-[3-(4-methyl-piperazin-1-ylmethyl)phenylamino]-pyrimidin-4-yl-urea (where, referring to formula IA, $R^1$ is 3-(4-methylpiperazin-1-ylmethyl)-phenylamino, $R^2$ is hydrogen, $R^3$ is methyl, $R^4$ is 2- and 6-chloro and 3- and 5-methoxy and n is 4, and $R^5$ is hydrogen), 3-(2,6-dichloro-3,5-dimethoxy-phenyl)-1-{6-[3-(4-ethyl-piperazin-1-yl)-phenylamino]-pyrimidin-4-yl}-1-methyl-urea (where, referring to formula IA, $R^1$ is 3-(4-ethyl-piperazin-1-yl)-phenylamino, $R^2$ is hydrogen, $R^3$ is methyl, $R^4$ is 2- and 6-chloro and 3- and 5-methoxy and n is 4, and $R^5$ is hydrogen), 3-(2,6-dichloro-3,5-dimethoxy-phenyl)-1-methyl-1-{6-[4-(2-morpholin-4-yl-ethoxy)phenylamino]-pyrimidin-4-yl}-urea (where, referring to formula IA, $R^1$ is 4-(2-morpholin-4-ylethoxy)-phenylamino, $R^2$ is hydrogen, $R^3$ is methyl, $R^4$ is 2- and 6-chloro and 3- and 5-methoxy and n is 4, and $R^5$ is hydrogen), 3-(2,6-dichloro-3,5-dimethoxy-phenyl)-1-{6-[4-(1-ethyl-piperidin-4-yl)-phenylamino]-pyrimidin-4-yl}-1-methyl-urea (where, referring to formula IA, $R^1$ is 4-(1-ethyl-piperidin-4-yl)phenylamino, $R^2$ is hydrogen, $R^3$ is methyl, $R^4$ is 2- and 6-chloro and 3- and 5-methoxy and n is 4, and $R^5$ is hydrogen), 3-(2,6-dichloro-3,5-dimethoxy-phenyl)-1-ethyl-1-{6-[4-(4-ethyl-piperazin-1-yl)-phenylamino]-pyrimidin-4-yl}-urea (where, referring to formula IA, $R^1$ is 4-(4-ethyl-piperazin-1-yl)-phenylamino, $R^2$ is hydrogen, $R^3$ is ethyl, $R^4$ is 2- and 6-chloro and 3- and 5-methoxy and n is 4, and $R^5$ is hydrogen) or 3-(2,6-dichloro-3,5-dimethoxy-phenyl)-1-{6-[4-(4-ethyl-piperazine-1-carbonyl)-phenylamino]-pyrimidin-4-yl}-1-methyl-urea (where, referring to formula IA, $R^1$ is 4-(4-ethyl-piperazine-1-carbonyl)-phenylamino, $R^2$ is hydrogen, $R^3$ is methyl, $R^4$ is 2- and 6-chloro and 3- and 5-methoxy and n is 4, and $R^5$ is hydrogen), (where in each of these compounds the moieties corresponding to $R^1$, $R^2$, $R^3$, $R^4$, $R^5$, X, Y and Z and n in formula IA are defined by the respective meanings as given for these compounds, respectively);

where in each of these compounds Y and Z are nitrogen and X is CH;

and in each case of a compound of the formula IA (as mentioned above or below) salts, prodrugs, N-oxides or esters thereof.

In one embodiment the present invention provides compounds of formula IA, wherein Y and Z are N (nitrogen) and X is CH, wherein either $R^1$ is 3-pyridyl which is monosubstituted by N—$C_1$-$C_7$-alkyl-piperazin-1-yl, $R^2$ is hydrogen, $R^3$ is hydrogen, each $R^4$ is, independently of the others, $C_1$-$C_7$-alkyl, halo-$C_1$-$C_7$-alkyl, halo or $C_1$-$C_7$-alkoxy, $R^5$ is hydrogen, and n is 1, 2, 3, 4 or 5.

In such embodiment, preferably $R^4$ is, independently of the others, halo or $C_1$-$C_7$-alkoxy, and n is preferably 3, 4 or 5, most preferably 4.

PREFERRED DEFINITIONS

The general terms used hereinbefore and hereinafter preferably have within the context of this disclosure the following meanings, unless otherwise indicated:

The prefix "lower" or "$C_1$-$C_7$" denotes a radical having up to and including a maximum of 7 in-chain atoms, especially up to and including a maximum of 4 in-chain atoms. Particular classes of alkyl and aliphatic comprise 1, 2, 3 or 4 carbon atoms. The radicals in question being either linear or branched with single or multiple branching.

Lower alkyl or $C_1$-$C_7$-alkyl is preferably alkyl with from and including 1 up to and including 7 carbon atoms, preferably 1, 2, 3 or 4 carbon atoms, and is linear or branched; for example, lower alkyl is butyl, such as n-butyl, sec-butyl, isobutyl, tert-butyl, propyl, such as n-propyl or isopropyl, ethyl or methyl. Exemplary lower alkyl is methyl, ethyl or isopropyl.

Where the plural form is used for compounds, salts, and the like, this is taken to mean also a single compound, salt, or the like.

Where phenyl is present in $R^1$ as ring binding $R^1$ to $NR^5$ in formula IA, the substituents hydroxy, phenyl-$C_1$-$C_7$-alkyloxy, piperazin-1-yl, 4-(phenyl-$C_1$-$C_7$-alkyl)-piperazin-1-yl; N-mono- or N,N-di-($C_1$-$C_7$-alkyl)-amino-$C_1$-$C_7$-alkyl, pyrrolidino-$C_1$-$C_7$-alkoxy, 1-($C_1$-$C_7$-alkyl)piperidin-4-yl, morpholino-$C_1$-$C_7$-alkoxy, thiomorpholino-$C_1$-$C_7$-alkoxy, 4-($C_1$-$C_7$-alkyl)piperazin-1-yl, [4-($C_1$-$C_7$-alkyl)-piperazin-1-yl]-$C_1$-$C_7$-alkyl, N-mono- or N,N-di-($C_1$-$C_7$-alkyl)-amino-$C_1$-$C_7$-alkyl, N-mono- or N,N-di-($C_1$-$C_7$-alkyl)-amino-$C_1$-$C_7$-alkoxy, [4-($C_1$-$C_7$-alkyl)piperazin-1-yl]-$C_1$-$C_7$-alkoxy, [4-($C_1$-$C_7$-alkyl)-piperazin-1-yl]-carbonyl are preferably present in the 3- or 4-position relative to the bond to $NR^3$.

Any asymmetric carbon atoms may be present in the (R)-, (S)- or (R,S)-configuration, preferably in the (R)- or (S)-configuration. Radicals having any unsaturation are present in cis-, trans- or (cis, trans) form. The compounds may thus be present as mixtures of isomers or as pure isomers, preferably as enantiomer-pure diastereomers.

The invention relates also to possible tautomers of the disclosed compounds.

In view of the close relationship between compounds of the formula IA in free form and in the form of their salts, including those salts that can be used as intermediates, for example in the purification or identification of the novel compounds, and tautomers or tautomeric mixtures and their salts, any reference hereinbefore and hereinafter to these compounds, is to be understood as referring also to the corresponding tautomers of these compounds, or salts of any of these, as appropriate and expedient and if not mentioned otherwise.

Tautomers can, e.g., be present in cases where amino or hydroxy, each with a least one bound hydrogen, are bound to carbon atoms that are bound to adjacent atoms by double bonds (e.g. keto-enol or imine-enamine tautomerism).

Where "a compound . . . , a tautomer thereof; or a salt thereof" or the like is mentioned, this means "a compound . . . , a tautomer thereof, or a salt of the compound and/or the tautomer".

Halogen (halo) is especially fluorine, chlorine, bromine, or iodine, especially (preferably in compounds of the formula I) fluorine, chlorine, or iodine.

Halo-$C_1$-$C_7$-alkyl means an $C_1$-$C_7$-alkyl wherein one or more hydrogen atoms are substituted by halogen atoms, e.g. trifluoromethyl.

[4-($C_1$-$C_7$-alkyl)-piperazin-1-yl]-carbonyl means [4-($C_1$-$C_7$-alkyl)-piperazin-1-yl]-C(=O)—.

The present invention relates to a compounds of Formula IA as described above and a salts, ester, N-oxide or prodrug thereof. In an aspect, therefore, the invention provides products which are compounds of Formula IA and/or salts, esters, N-oxides or prodrugs thereof.

Salts are especially the pharmaceutically acceptable salts of compounds of Formula IA (or exemplary formula thereof), especially if they are forming salt-forming groups.

Salt-forming groups are groups or radicals having basic or acidic properties. Compounds having at least one basic group or at least one basic radical, for example basic nitrogen, such as amino, a secondary amino group not forming a peptide bond or tertiary amino, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or polyacid addition salts may be formed.

Compounds having acidic groups, a carboxy group or a phenolic hydroxy group, may form metal or ammonium-salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

In view of the close relationship between the novel compounds or N-oxides thereof in free form and those in the form of their salts, including those salts that can be used as intermediates, for example in the purification or identification of the novel compounds, any reference to the free compounds (including compounds of the formula IA, intermediates and starting materials) hereinbefore and hereinafter is to be understood as referring also to the corresponding N-oxides, and/or salts, hydrates, solvates and/or crystal forms of the compounds or their N-oxides, as appropriate and expedient.

The compounds of formula IA (or exemplary formulae thereof) have valuable pharmacological properties, as described hereinbefore and hereinafter.

Biology

The efficacy of the compounds of the invention as inhibitors of Bcr-Abl, c-KIT, EphB4, EGF-R, VEGF-R2 (KDR), FGF-R, Tie-2 (Tek), Ret, PDGFR, raf, FLT3, c-src and/or FGFR3 receptor tyrosine kinase activity can be demonstrated as follows.

In the following, "inhibitors", "active compounds" or the like refers to compounds of the formula IA.

Test for Activity Against Bcr-Abl:

The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institue, Bosten, Mass., USA). The cells express the fusion Bcr-Abl protein with a constitutively active abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of $2 \times 10^6$ cells per vial in freezing medium (95% FCS, 5% DMSO (SIGMA)). After thawing, the cells are used during maximally 10-12 passages for the experiments. The antibody anti-abl SH3 domain cat. #06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. #03-7722) is used. As comparison and reference compound, (N-{5-[4-4-methyl-piperazino-methyl)-benzoylamido]-2-methylphenyl}-4-(3-pyridyl)-2-pyrimidine-amine, in the form of the methane sulfonate (monomesylate) salt (STI571) (marketed as Gleevec® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 µM followed by preparation of serial threefold dilutions in complete medium. No solubility problems are encountered using this procedure. The test compounds are treated analogously. For the assay, 200'000 32D-bcr/abl cells in 50 µl are seeded per well in 96 well round bottom tissue culture plates. 50 µl per well of serial threefold dilutions of the test compound are added to the cells in triplicates. The final concentration of the test compound range e.g. from 5 µM down to 0.01 µM. Untreated cells are used as control. The compound is incubated together with the cells for 90 min at 37° C., 5% CO$_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/ml aprotinin and 80 µg/ml leupeptin) and either used immediately for the ELISA or stored frozen at −20° C. until usage. The anti-abl SH3 domain antibody is coated at 200 ng in 50 µl PBS per well to black ELISA plates (Packard HTRF-96 black plates; 6005207) overnight at 4° C. After washing 3× with 200 Siwell PBS containing 0.05% Tween 20 (PBST) and 0.5% TopBlock (Juro, Cat. #TB 232010), residual protein binding sites are blocked with 200 µl/well PBST, 3% TopBlock for 4 h at room temperature, followed by incubation with 50 µl lysates of untreated or test compound-treated cells (20 µg total protein per well) for 3-4 h at 4° C. After 3× washing, 50 µl/well PY20(AP) (Zymed) diluted to 0.5 µg/ml in blocking buffer is added and incubated overnight (4 IC). For all incubation steps, the plates are covered with plate sealers (Costar, cat. #3095). Finally, the plates are washed another three times with washing buffer and once with deionized water before addition of 90 µl/well of the AP substrate CPDStar RTU with Emerald II. The plates now sealed with Packard Top Seal™-A plate sealers (cat. #6005185) are incubated for 45 min at room temperature in the dark and luminescence is quantified by measuring counts per second (CPS) with a Packard Top Count Microplate Scintillation Counter (Top Count). For the final optimized version of the ELISA, 50 µl of the lysates of the cells grown, treated and lysed in 96 well tissue culture plates, are transferred directly from these plates to the ELISA plates that are precoated with 50 ng/well of the rabbit polyclonal ant-abl-SH3 domain AB 06-66 from Upstate. The concentration of the anti-phosphotyrosine AB PY20 (AP) can be reduced to 0.2 µg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the IC$_{50}$ are determined from the dose response curves by graphical inter- or extrapolation. The compounds of the invention here preferably show IC$_{50}$ values in the range from 15 nM to 500 µM, most preferably 15 nM to 200 µM.

For cellular assays, compounds are dissolved in DMSO and diluted with complete medium to yield a starting concentration of 10 µM followed by preparation of serial 3-fold dilutions in complete medium. 32D or Ba/F3 cells expressing either 'wt'-Bcr-Abl or Bcr-Abl mutants (e.g. T-315-I) were seeded at 200'000 cells in 50 µL complete medium are seeded per well in 96 well round bottom tissue culture plates. 50 µL per well of serial 3-fold dilutions of the test compound are added to the cells in triplicates. Untreated cells are used as control. The compound is incubated together with the cells for 90 min at 37° C., 5% CO$_2$, followed by centrifugation of the tissue culture plates at 1300 rpm (Beckmann GPR centrifuge) and removal of the supernatants by careful aspiration taking care not to remove any of the pelleted cells. The cell pellets are lysed by addition of 150 µL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 µg/mL aprotinin and 80 µg/mL leupeptin) and either used immediately for the ELISA or stored frozen in the plates at −20° C. until usage.

The rabbit polyclonal anti-abl-SH3 domain Ab 06-466 from Upstate was coated at 50 ng in 50 µl PBS per well to black ELISA plates (Packard HTRF-96 black plates; 6005207) over night at 4° C. After washing 3 times with 200 µL/well PBS containing 0.05% Tween20 (PBST) and 0.5% TopBlock (Juro), residual protein binding sites are blocked with 200 µL/well PBST, 3% TopBlock for 4 h at room temperature followed by incubation with 50 L lysates of untreated or compound-treated cells (20 µg total protein per well) for 3-4 h at 4° C. After 3 washings, 50 µL/well anti-phosphotyrosine Ab PY20(AP) labeled with alkaline phosphatase (Zymed) diluted to 0.2 µg/mL in blocking buffer is added and incubated over night (4° C.). For all incubation steps the plates are covered with plate sealers (Costar). Finally, the plates are washed another three times with washing buffer and once with deionized water before addition of 90 µL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count).

The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ (and $IC_{90}$) are determined from the dose response curves by graphical extrapolation.

The compounds of the invention here can preferably show $IC_{50}$ values in the range from 50 nM to 500 µM for inhibition of autophosphorylation and inhibition of IL-3 independent proliferation of Bcr-Abl mutants in Ba/F3 transfected cells, in particular T315I.

The 32D cl3 cells are obtained from the American Type Culture Collection (ATCC CRL11346) and the Ba/F3 cells from the German Collection of Microorganisms and Cell Cultures (DSMZ, Braunschweig and DSMZ No. ACC 300) Palacios et al., *Nature,* 309: 1984, 126, PubMed ID 6201749. Palacios et al., *Cell,* 41: 1985, 727, PubMed ID 3924409

The Ba/F3.p210 cells and the murine hematopoietic 32D cl3cells, (32D p210 cells) are obtained by transfecting the IL-3-dependent murine hematopoietic Ba/F3 cell line with a pGD vector containing p21 OBCR-ABL (B2A2) cDNA Daley and Baltimore, 1988; Sattler et al., 1996; Okuda et al., 1996.

Daley, G. Q., Baltimore, D. (1988) Transformation of an interleukin 3-dependent hematopoietic cell line by the chronic myeloid leukemia-specific p210 BCR-ABL protein. *PNAS* 85, 9312-9316.

Sattler M, Salgia R, Okuda K, Uemura N, Durstin M A, Pisick E, et al. (1996) The protooncogene product p120CBL and the adaptor proteins CRKL and c-CRK link c-ABL, p190BCR-ABL and p210BCR-ABL to the phosphatidylinositol-3' kinase pathway. *Oncogene* 12, 839-46.

Okuda K, Golub T R, Gilliland D G, Griffin J D. (1996) p210BCR-ABL, p190BCR-ABL, and TEL/ABL activate similar signal transduction pathways in hematopoietic cell lines. *Oncogene.* 13, 1147-52.

Test for Activity Against c-KIT

The baculovirus donor vector pFbacG01 GIBCO is used to generate a recombinant baculovirus that expresses the amino acid region amino acids 544-976 of the cytoplasmic kinase domains of human c-Kit. The coding sequences for the cytoplasmic domain of c-Kit is amplified by PCR from a human uterus c-DNA library (Clontech). The amplified DNA fragment and the pFbacG01 vector are made compatible for ligation by digestion with BamH1 and EcoRI. Ligation of these DNA fragments results in the baculovirus donor plasmid c-Kit. The production of the viruses, the expression of proteins in Sf9 cells and the purification of the GST-fused proteins are performed as follows:

Production of virus: Transfer vector pFbacG01-c-Kit containing the c-Kit kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 cells or Sf21 cells American Type Culture Collection are then transfected in 25 cm² flasks with the viral DNA using Cellfectin reagent.

Determination of small scale protein expression in Sf9 cells: Virus containing media is collected from the transfected cell culture and used for infection to increase its titer. Virus containing media obtained after two rounds of infection is used for large-scale protein expression. For large-scale protein expression 100 cm² round tissue culture plates are seeded with $5 \times 10^7$ cells/plate and infected with 1 mL of virus-containing media (approx. 5 MOIs). After 3 days the cells are scraped off the plate and centrifuged at 500 rpm for 5 min. Cell pellets from 10-20, 100 cm² plates, are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged protein: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged protein is eluted by 10 applications (1 mL each) of 25 mM Tris-HCl, pH 7.5, 10 mM reduced-glutathione, 100 mM NaCl, 1 mM DTT, 10% Glycerol and stored at −70° C.

Kinase assay: Tyrosine protein kinase assays with purified GST-c-Kit are carried out in a final volume of 30 µL containing 200-1800 ng of enzyme protein (depending on the specific activity), 20 mM Tris-HCl, pH 7.6, 3 mM $MnCl_2$, 3 mM $MgCl_2$, 1 mM DTT, 10 µM $Na_3VO_4$, 5 µg/mL poly(Glu,Tyr) 4:1, 1% DMSO, 1.0 µM ATP and 0.1 µCi [$\gamma^{33}$ P] ATP. The activity is assayed in the presence or absence of inhibitors, by measuring the incorporation of $^{33}P$ from [$\gamma^{33}P$] ATP into the poly(Glu,Tyr) 4:1 substrate. The assay (30 µL) is carried out in 96-well plates at ambient temperature for 20 min under conditions described below and terminated by the addition of 20 µL of 125 mM EDTA. Subsequently, 40 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed 4× on a shaker with 1.0% $H_3PO_4$ and once with ethanol. Membranes are counted after drying at ambient temperature, mounting in Packard TopCount 96-well frame, and addition of 10 µL/well of Microscint™ (Packard). $IC_{50}$ values are calculated by linear regression analysis of the percentage inhibition of each compound in duplicate, at four concentrations (usually 0.01, 0.1, 1 and 10 µM). One unit of protein kinase activity is defined as 1 nmole of $^{33}P$ ATP transferred from [$\gamma^{33}P$] ATP to the substrate protein per minute per mg of protein at 37° C. $IC_{50}$ values ranging preferably between 50 nM to 500 µM can be found with a compound of the formula IA according to the invention.

Test for Activity Against EphB4

The efficacy of compounds of the formula IA as inhibitors or Ephrin B4 receptor (EphB4) kinases can be demonstrated as follows:

Generation of Bac-to-Bac™ (Invitrogen Life Technologies, Basel, Switzerland) GST-fusion expression vectors: Entire cytoplasmatic coding regions of the EphB-class are amplified by PCR from cDNA libraries derived from human placenta or brain, respectively. Recombinant baculovirus are generated that express the amino acid region 566-987 of the human EphB4 receptor (SwissProt Database, Accession No.

P54760). GST sequence is cloned into pFastBac1® vector (Invitrogen Life Technologies, Basel, Switzerland) and PCR amplified. cDNAs encoding EphB4-receptor domains, respectively are cloned in frame 3'prime to the GST sequence into this modified FastBac1 vector to generate pBac-to-Bac™ donor vectors. Single colonies arising from the transformation are inoculated to give overnight cultures for small scale plasmid preparation. Restriction enzyme analysis of plasmid DNA reveals several clones to contain inserts of the expected size. By automated sequencing the inserts and approximately 50 bp of the flanking vector sequences are confirmed on both strands.

Production of viruses: Viruses for each of the kinases are made according to the protocol supplied by GIBCO if not stated otherwise. In brief, transfer vectors containing the kinase domains are transfected into the DH10Bac cell line (GIBCO) and plated on selective agar plates. Colonies without insertion of the fusion sequence into the viral genome (carried by the bacteria) are blue. Single white colonies are picked and viral DNA (bacmid) isolated from the bacteria by standard plasmid purification procedures. Sf9 cells or Sf21 cells are then transfected in 25 cm$^2$ flasks with the viral DNA using Cellfectin reagent according to the protocol.

Purification of GST-tagged kinases: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Protein kinase assays: The activities of protein kinases are assayed in the presence or absence of inhibitors, by measuring the incorporation of $^{33}$P from [γ$^{33}$P]ATP into a polymer of glutamic acid and tyrosine (poly(Glu,Tyr)) as a substrate. The kinase assays with purified GST-EphB (30 ng) are carried out for 15-30 min at ambient temperature in a final volume of 30 μL containing 20 mM Tris-HCl, pH 7.5, 10 mM MgCl$_2$, 3-50 mM MnCl$_2$, 0.01 mM Na$_3$VO$_4$, 1% DMSO, 1 mM DTT, 3 μg/mL poly(Glu,Tyr) 4:1 (Sigma; St. Louis, Mo., USA) and 2.0-3.0 μM ATP (γ-[$^{33}$P]-ATP 0.1 μCi). The assay is terminated by the addition of 20 μL of 125 mM EDTA. Subsequently, 40 μl of the reaction mixture are transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μl 0.5% H$_3$PO$_4$. Membranes are removed and washed 4× on a shaker with 1.0% H$_3$PO$_4$, once with ethanol. Membranes are counted after drying at ambient temperature, mounting in Packard TopCount96-well frame, and addition of 10 μL/well of Microscint™ (Packard). IC$_{50}$ values are calculated by linear regression analysis of the percentage inhibition of each compound in duplicate, at four concentrations (usually 0.01, 0.1, 1 and 10 μM). One unit of protein kinase activity is defined as 1 nmole of $^{33}$P ATP transferred from [γ$^{33}$P] ATP to the substrate protein per minute per mg of protein at 37° C. IC$_{50}$ values preferably ranging from 50 nM to 500 μM can be found with compounds of the formula IA according to the invention.

Test for Activity Against EGF-R:

The inhibition of EGF-R tyrosine kinase activity can be demonstrated using known methods, for example using the recombinant intracellular domain of the EGF-receptor [EGF-R ICD; see, for example, E. McGlynn et al., Europ. J. Biochem. 207, 265-275 (1992)]. Compared with the control without inhibitor, the compounds of formula IA inhibit the enzyme activity by 50% (IC$_{50}$), for example in a concentration of from 0.05 to 500 μM.

As well as or instead of inhibiting EGF-R tyrosine kinase activity, the compounds of formula IA also inhibit other members of this family of receptors, like ErbB-2. The inhibitory activity (IC$_{50}$) is approximately in the range of 0.01 to 500 μM. The inhibition of ErbB-2 tyrosine kinase (HER-2) can be determined, for example, analogously to the method used for EGF-R protein tyrosine kinase [see C. House et al., Europ. J. Biochem. 140, 363-367 (1984)]. The ErbB-2 kinase can be isolated, and its activity determined, by means of protocols known per se, for example in accordance with T. Akiyama et al., Science 232, 1644 (1986).

Test for Activity Against VEGF-R2 (KDR):

The inhibition of VEGF-induced receptor autophosphorylation can be confirmed with a further in vitro experiments in cells such as transfected CHO cells, which permanently express human VEGF-R2 receptor (KDR), are seeded in complete culture medium (with 10% fetal calf serum=FCS) in 6-well cell-culture plates and incubated at 37° C. under 5% CO$_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. #TB232010) in phosphate buffered saline with Tween 20® (polyoxyethylen (20)sorbitane monolaurate, ICI/Uniquema) (PBST). The cell lysates (20 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the IC$_{50}$ (inhibitory dose for 50% inhibition). IC$_{50}$ values preferably ranging from 20 nM to 500 μM can be found with compounds of the formula IA according to the invention.

Test for Activity Against Recombinant Protein Kinases Ret (Ret-Men2A), Tie-2 (Tek) and FGFR3-K650E:

Cloning and expression of recombinant protein kinases: (Ret); The Baculovirus donor vector pFB-GSTX3 is used to generate a recombinant Baculovirus that expresses the amino acid region 658-1072 of the intra-cytoplasmic kinase domain of human Ret-Men2A which corresponds to the wild type kinase domain of Ret. The coding sequence for the cytoplasmic domain of Ret is amplified by PCR from the plasmid pBABEpuro RET-Men2β which is received from Dr. James Fagin, College of Medicine, University of Cincinnati (Novartis collaboration). The amplified DNA fragments and the pFB-GSTX3 vector are made compatible for ligation by digestion with SalI and KpnI. Ligation of these DNA fragments result in the baculovirus donor plasmid pFB-GX3-Ret (-Men2A).

(Tie-2/Tek): The baculovirus donor vector pFbacG01 is used to generate a recombinant baculovirus that expressed the amino acid region amino acids 773-1124 of the cytoplasmic kinase domain of human Tek, N-terminally fused to GST (Provided by Dr. Marmé, Institute of Molecular Medicine, Freiburg, Germany based on a Research Collaboration). Tek is recloned into the pFbacG01 transfer vector by EcoRI excision and ligation into EcoRI digested pFbacG01 (FBG-Tie2/Tek).

(FGFR-3-K650β): The baculovirus donor vector pFast-BacGST2 is used to generate a recombinant baculovirus that expresses the amino acid (aa) region amino acids 411-806 of the cytoplasmic domain of human FGFR-3, N-terminally fused to GST (Provided by Dr. Jim Griffin, Dana Farber Cancer Institute, Boston, USA based on a Research Collaboration). DNA encoding amino acids 411-806 is amplified by PCR, inserted into the pFastBac-GT2 vector to yield pFB-GT2-FGFR3-wt. This plasmid is in turn used to generate a vector encoding FGFR3(411-806) with a mutation at K650 using the Stratagene XL-Site directed Mutagenesis Kit to produce pFB-GT2-FGFR3—K650E. The production of the viruses, the expression of proteins in Sf9 cells and the purification of the GST-fused proteins are performed as described in the following sections.

Production of virus: Transfer vectors containing the kinase domains are transfected into the DH10Bac cell line (GIBCO) and plated on selective agar plates. Colonies without insertion of the fusion sequence into the viral genome (carried by the bacteria) are blue. Single white colonies are picked and viral DNA (bacmid) isolated from the bacteria by standard plasmid purification procedures. Sf9 cells or Sf21 cells are then transfected in 25 cm² flasks with the viral DNA using Cellfectin reagent.

Determination of small scale protein expression in Sf9 cells: Virus containing medium is collected from the transfected cell culture and used for infection to increase its titer. Virus containing media obtained after two rounds of infection are used for large-scale protein expression. For large-scale protein expression 100 cm² round tissue culture plates are seeded with 5×10⁷ tells/plate and infected with 1 mL of virus-containing medium (approx. 5 MOIs). After 3 days the cells are scraped off the plate and centrifuged at 500 rpm for 5 min. Cell pellets from 10-20, 100 cm² plates, are resuspended in 50 mL of ice-cold lysis buffer (25 mM Tris-HCl, pH7.5, 2 mMEDTA, 1% NP40, 1 mM DTT, 1 mMPSF). The cells are stirred on ice for 15 min and then centrifuged at 5000 rpms for 20 min.

Purification of GST-tagged proteins: The centrifuged cell lysate is loaded onto a 2 mL glutathione-sepharose column and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Measure of enzyme activity: Tyrosine protein kinase assays with either purified GST-Ret, GST-Tek or GST-FGFR-3-K650E are carried out in a final volume of 30 µL with final concentrations of the following components: Ret included 15 ng of GST-Ret, 20 mM Tris-HCl, pH 7.5, 1 mM MnCl$_2$, 10 mM MgCl$_2$, 1 mM DTT, 3 µg/mL poly(Glu,Tyr) 4:1, 1% DMSO and 2.0 µM ATP (γ-[$^{33}$P]-ATP 0.1 µCi). Tek included 150 ng of GST-Tek, 20 mM Tris-HCl, pH 7.5, 3 mM MnCl$_2$, 3 mM MgCl$_2$, 1 mM DTT, 0.01 mM Na$_3$VO$_4$, 250 µg/mL PEG 20'000, µg/mL poly(Glu,Tyr) 4:1, 1% DMSO and 4.0 µM ATP (γ-[$^{33}$P]-ATP 0.1 µCi). FGFR-3-K650E included 10 ng of GST-FGFR-3-K650E, 20 mM Tris-HCl, pH 7.5, 3 mM MnCl$_2$, 3 mM MgCl$_2$, 1 mM DTT, 0.01 mM PEG 20'000, 10 µg/mL poly(Glu,Tyr) 4:1, 1% DMSO and 4.0 µM ATP (γ-[$^{33}$P]-ATP 0.1 µCi). The activity is assayed in the presence or absence of inhibitors, by measuring the incorporation of $^{33}$P from [γ$^{33}$P] ATP into poly(Glu,Tyr) 4:1. The assay is carried out in 96-well plates at ambient temperature for 30 min under conditions described below and terminated by the addition of 50 µL of 125 mM EDTA. Subsequently, 60 µL of the reaction mixture are transferred onto Immobilon-PVDF membrane (Millipore) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 µL 0.5% H$_3$PO$_4$. Membranes are removed and washed 4× on a shaker with 1.0% H$_3$PO$_4$, once with ethanol. Membranes are counted after drying at ambient temperature, mounting in Packard TopCount 96-well frame, and addition of 10 µL/well of Microscint™ (Packard). IC50 values are calculated by linear regression analysis of the percentage inhibition of each compound in duplicate, at four concentrations (usually 0.01, 0.1, 1 and 10 µM). One unit of protein kinase activity is defined as 1 nmole of $^{33}$P ATP transferred from [γ$^{33}$P] ATP to the substrate protein per minute per mg of protein at 37° C. IC$_{50}$ values preferably ranging from 50 nM to 500 µM can be found with compounds of the formula IA according to the invention.

FGFR3 (Enzymatic Assay)

Kinase activity assay with purified FGFR3 (Upstate) is carried out in a final volume of 10 µL containing 0.25 µg/mL of enzyme in kinase buffer (30 mM Tris-HCl pH7.5, 15 mM MgCl$_2$, 4.5 mM MnCl$_2$, 15 µM Na$_3$VO$_4$ and 50 µg/mL BSA), and substrates (5 µg/mL biotin-poly-EY (Glu, Tyr) (CIS-US, Inc.) and 3 µM ATP). Two solutions are made: the first solution of 5 µl contains the FGFR3 enzyme in kinase buffer was first dispensed into 384-format ProxiPlate® (Perkin-Elmer) followed by adding 50 mL of compounds dissolved in DMSO, then 5 µl of second solution contains the substrate (poly-EY) and ATP in kinase buffer is added to each wells. The reactions are incubated at room temperature for one hour, stopped by adding 10 µL of HTRF detection mixture, which contains 30 mM Tris-HCl pH7.5, 0.5 M KF, 50 mM ETDA, 0.2 mg/mL BSA, 15 µg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). IC$_{50}$ values are calculated by linear regression analysis of the percentage inhibition of each compound at 12 concentrations (1:3 dilution from 50 µM to 0.28 nM). In this assay, compounds of the invention, for example, can preferably have an IC$_{50}$ in the range of 2 nM to 400 µM, more preferably in the range of 5 nM to 100 µM.

FGFR3 (Cellular Assay)

Compounds of the invention (=of the formula IA) are tested for their ability to inhibit trans-formed Ba/F3-TEL- FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsufoxide (DMSO). Twelve points 1:3 serial dilutions are made into DMSO to create concentrations gradient ranging typically from 10 mM to 0.05 µM. Cells are added with 50 mL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations. $IC_{50}$ values preferably ranging from 2 nM to 400 µM can be found with a compound of the formula IA according to the invention.

Upstate KinaseProfiler—Radio-Enzymatic Filter Binding Assay

Compounds of the invention are assessed for their ability to inhibit individual members of a panel of kinases (a partial, non-limiting list of kinases includes: Abl, BCR-Abl, BMX, FGFR3, Lck, JNK1, JNK2, CSK, RAF, MKK6 and P38). The compounds are tested in duplicates at a final concentration of 10 µM following this generic protocol. Note that the kinase buffer composition and the substrates vary for the different kinases included in the "Upstate KinaseProfiler™" panel. The compounds are tested in duplicates at a final concentration of 10 µM following this generic protocol. Note that the kinase buffer composition and the substrates vary for the different kinases included in the "Upstate KinaseProfiler™" panel. Kinase buffer (2.5 □L, 10× containing $MnCl_2$ when required), active kinase (0.001-0.01 Units; 2.5 µL), specific or Poly(Glu4-Tyr) peptide (5-500 □M or 0.01 mg/ml) in kinase buffer and kinase buffer (50 □M; 5 □L) are mixed in an eppendorf on ice. A Mg/ATP mix (10 □L; 67.5 (or 33.75) mM $MgCl_2$, 450 (or 225) µM ATP and 1 µCi/µl [γ-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

The compounds of formula IA can also inhibit other tyrosine protein kinases such as especially the c-Src kinase which plays a part in growth regulation and transformation in animals, especially mammal cells, including human cells. An appropriate assay is described in Andre-jauskas-Buchdunger et al., Cancer Res. 52, 5353-8 (1992). Using this test system, compounds of the formula IA can show $IC_{50}$ values for inhibition of c-Src in the range of e.g. 0.05 to 500 µM.

Further, compounds of the formula IA can also be used to inhibit b-raf (V599E). The activity of B-Raf-V599E is assayed in the presence or absence of inhibitors measuring the incorporation of $^{33}$P from [γ$^{33}$P]ATP into (His)-IκB. The test compound is dissolved in DMSO (10 mM) and stored at −20° C. Serial dilutions are made in DMSO freshly and further diluted with pure water to obtain 3 times concentrated test solutions in 3% DMSO. The final volume (30 µl) of the assay contains 10 µl of test solution (1% DMSO), 10 µl assay mix (20 mM Tris-HCl, pH 7.5, 3 mM $MnCl_2$, 3 mM $MgCl_2$, 1 nM DTT, 3 µg/ml (His)-IκB. 1% DMSO and 3.5 µM ATP [γ$^{33}$P]-ATP 0.1 µCi) and 10 µl enzyme dilution (600 ng of GST-B-Raf-V599E). The pipetting steps are programmed to be performed either on the MultiPROBE Iix, MultiPROBE IILx or HamiltonSTAR robots in the 96-well format. The assay is carried out as described in the literature (see C. Garcia-Echeverria et al., Cancer Cel. 5, 231-9 (2004)) terminated by the addition of 20 µl 125 mM EDTA. The capturing of the phosphorylated peptides by the filter binding method is performed as following: 40 µl of the reaction mixture are transferred onto Immobilon-PVDF membranes previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µl 0.5% $H_3PO_4$. Free membranes are removed and washed 4× on a shaker with 1.0% $H_3PO_4$, once with ethanol. Membranes are counted after drying at ambient temperature, mounting in Packard TopCount 96 well frame and addition of 10 µl/well of Microscint™. The plates are eventually sealed and counted in a microplate scintillation counter (TopCoupt NXT, TopCount NXT HTS). In case of the flash plate method, the kinase reaction is first carried out in polystyrene-based plastic plates and then stopped after 60 min by the addition of 20 µl of 125 mM EDTA. For capturing (60 min, RT), the biotinylated substrate is transferred to Nickel-coated flash plates. The assay plates are washed three times with PBS and dried at room temperature. Afterwards, the plates are sealed and counted in a microplate scintillation counter (TopCount NXT, TopCount NXT HTS). $IC_{50}$ values are calculated by linear regression analysis of percentage inhibition by the compound either in duplicate, at four concentrations (usually 0.01, 0.1, 1 and 10 µM) or as 8 single point $IC_{50}$ starting at 10 µM followed by 1:3 dilutions. For b-raf inhibition, compounds of the formula IA preferably can show $IC_{50}$ values in the range from 0.05 to 500 µM.

FLT3 Receptor Kinase

To search for FLT3-targeted compounds, two different kinds of assays can be employed:

Flt3 kinase activity is determined as follows: The baculovirus donor vector pFbacG01 (GIBCO) is used to generate a recombinant baculovirus expressing the amino acid region from amino acids 563-993 of the cytoplasmic kinase domain of human Flt3. The coding sequence for the cytoplasmic domain of Flt3 is amplified by PCR from human c-DNA libraries (Clontech). The amplified DNA fragments and the pFbacG01 vector are made compatible for ligation by digestion with BamHI and HindIII. Ligation of these DNA fragments results in the baculovirus donor plasmid Flt-3(1.1). The production of the viruses, the expression of protein in Sf9 cells and the purification of the GST-fused protein is performed as follows:

Production of virus: Transfer vector (pFbacG01-Flt-3) containing the Flt3-kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 or Sf21 cells (American Type Culture Collection) are then transfected in flasks with the viral DNA using Cellfectin reagent.

Determination of small scale protein expression on Sf9 cells: Virus containing medium is collected from the transfected cell culture and used for infection to increase its titre. Virus containing medium obtained after two rounds of infection is sued for large-scale protein expression. For large-scale protein expression, 100 cm$^2$ round tissue culture plates are seeded with 5×10$^7$ cells/plate and infected with 1 ml of virus-containing medium (approximately 5 MOIs). After 3 days, the cells are scraped off the plate and centrifuged at 500 rpm for 5 min. Cell pellets from 10-20 plates with each 100 cm$^2$ are re-suspended in 50 ml of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpm for 20 min.

Purification of GST-tagged protein: The centrifuged cell lysate is loaded onto a 2 ml glutathione-sepharose column (Pharmacia) and washed three times with 10 ml of 25 mM Tris-HCl, pH 7.5, 2 mM EDTA, 1 mM DTT; 200 mM NaCl. The GST-tagged protein is then eluted by 10 applications (1 ml each) of 25 mM Tris-HCl, pH 7.5, 10 mM reduced glutathione, 100 mM NaCl, 1 mM DTT, 10% glycerol, and stored at −70° C.

Measurement of Enzyme activity: Tyrosine protein kinase assays with purified GST-Flt2 are carried out in a final volume of 30 µl containing 200-1800 ng of enzyme protein (depending on the specific activity), 20 mM Tris-HCl, pH 7.6, 3 mM MnCl$_2$, 3 mM MgCl$_2$, 1 mM DTT, 10 µM Na$_3$VO$_4$, 3 µg/ml poly(Glu,Tyr) 4:1, 1% DMSO, 6.0 µM ATP and 0.1 µCi [$\gamma^{33}$P]ATP. The activity is assayed in the presence or absence of inhibitors, by measuring the incorporation of $^{33}$P from [$\gamma^{33}$P]ATP into the poly(Glu,Tyr) substrate. The assay (30 µl per well) is carried out in 96-well plates at ambient temperature for 20 min under conditions described below and terminated by the addition of 20 µl of 125 mM EDTA. Subsequently, 40 µl of each reaction mixture is transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 µl 0.5% H$_3$PO$_4$. Membranes are removed and washed 4× on a shaker with 1.0% H$_3$PO$_4$, once with ethanol. Membranes are then counted individually after drying at ambient temperature, mounting in Packard TopCount 96-well frame and addition of 10 µl/well Microscint™ (Pakard). IC$_{50}$ values are calculated by linear regression analysis of the percentage inhibition of each compound in duplicate, at four concentrations (usually 0.01, 0.1, 1 and 10 µM). One unit of protein kinase is defined as 1 nmole of $^{33}$P ATP transferred from [$\gamma^{33}$P]ATP to the substrate polypeptide per minute per mg of protein at 37° C. The compounds of the formula IA here preferably can show IC$_{50}$ values in the range between 0.05 and 500 µM.

Alternatively or in addition, a cell based assay can be utilised to identify inhibitors of mutant FLT3 tyrosine kinase receptors. The general technique involves comparing the effects of possible inhibitors on cell lines that depended on mutant FLT3 for proliferation, versus cell lines that do not depend on mutant FLT3 for proliferation. Cell lines expressing two different forms of mutated, activated FLT3 are used:

Ba/F3-FLT3-ITD cells expressing a FLT3 mutant with an 'Internal Tandem Duplication' (ITD) within the juxtamembrane domain of the receptor.

Ba/F3-FLT3-D835Y cells expressing an FLT3 receptor containing a mutation converting Asparagine at position 835 to Tyrosine.

Preferably compounds of the formula IA can be shown to inhibited proliferation of both Ba/F3-FLT3-ITD and Ba/F3-D835Y cells at an IC50 of 50 nM to 500 µM while on the other hand they usually do not inhibit growth of untransformed Ba/F3 cells at concentrations of up to 500 nM, and the growth inhibitory effects of a compound of the formula IA on Ba/F3-FLT3-ITD cells can be reversed by the addition of high concentrations of IL-3 to provide an alternative viability signal. At the concentrations required to inhibit the proliferation of FLT3-dependent cell-lines, compounds of the formula IA can be shown to be not cytotoxic against several human leukemia and lymphoma cell lines' that do not have mutant FLT3 receptors (hyperactivated kinases), suggesting that the drug has an unexpected high degree of specificity as a cytoxic agent. Overall, these results indicate that compounds of the formula IA can be potent inhibitors of mutant FLT3 receptor tyrosine kinase activity and are a promising candidate for use in the treatment in patients with mutant FLT3 receptors. In particular, compounds of the formula IA can be shown inhibits the activity of FLT3 receptor tyrosine kinase activity in concentrations in the range of 0.05 to 500 µM.

On the basis of the inhibitory studies hereinbefore described, a compound of Formula IA or (or exemplary formula thereof) according to the invention shows therapeutic efficacy especially against disorders dependent on (=especially responding to modulation, more specifically inhibition of) protein kinase, especially proliferative diseases, such as the diseases mentioned above under "Background of the invention".

There are also experiments to demonstrate the antitumor activity of compounds of the formula I in vivo. For example, in order to test whether a compound of the formula IA inhibits the growth of bladder carcinoma, the following test system can be applied:

The RT-112 human urinary bladder transitional cell carcinoma cell line is used as an in vivo model for the testing of in vivo activity of compounds described in the invention. This cell line is derived from a female patient (age unknown) with untreated primary urinary bladder carcinoma in 1973. This cell line expresses high levels of FGF-R3.

5×10$^6$ cells with matrigel are inoculated subcutaneously in the flank of female nude mice (n=8) and tumors are allowed to develop. Tumor sizes are measured manually every two to three days using a caliper. Animal weight is monitored as a measure of animal health.

Treatment with inhibitor starts when tumors volumes reach ~100 mm$^3$ (~7 days). Mice are randomized according to tumor volume and treated with vehicle (NMP/PEG300) or the test compound (n=8) for 14 days. Route of administration is oral gavage and schedule is 1× day/7× week. Antitumor activity is calculated as T/C % ((mean change tumor volume of treated animals/mean change of tumor volumes of control animals)×100).

Xenograft tumor sizes are measured manually with calipers and tumor-volume are estimated using the formula (W×H×L)×π/6, where width (W), height (H) and length (L) are the three largest diameters.

Statistical evaluations are done using SigmaStat 2.03. If more than two groups of animals are included in an experiment, the statistical evaluation is done on the absolute tumor volumes or body weights on the evaluation day, using one-way ANOVA test. Dunnett's ad hoc post test is used when a control group is compared with all other treatment groups. Tukey and SNK (Student-Newman-Keuls) ad hoc post test are used when all groups are evaluated against each other.

Tumor samples are dissected and snap frozen in liquid N$_2$. Tumors are pulverized while maintained frozen. An aliquot of the frozen powder is lysed in 1% triton extraction buffer containing protease and phosphatase inhibitors. Lysates are cleared by centrifugation and protein concentration determined. Protein lysate is used to determined the degree of inhibition of the FGFR receptor and pathway in the tumors.

Compounds of the formula IA described in this invention can inhibit tumor growth and induce regression at doses equal and above 10 mg/kg.

As examples of kinases inhibited by the compounds of the formula IA as disclosed may be mentioned c-Abl and Bcr-Abl, in particular, inhibition of Bcr-Abl may be mentioned. Another inhibited kinase is the receptor tyrosine kinase VEGF-R, in particular the VEGF receptor KDR (VEGF-R2). The compounds of the present invention also inhibit mutant forms of the Bcr-Abl kinases. The disclosed compounds are appropriate for the inhibition of one or more of these and/or other protein tyrosine kinases and/or the non-receptor tyrosine kinase Raf, and/or for the inhibition of mutants of these enzymes. In view of these activities, the compounds can be used for the treatment of diseases related to, especially, aberrant or excessive activity of such types of kinases, especially those mentioned.

The ability to modulate such protein kinase activity preferably relates to the inhibition of such protein kinase activity.

For example, as inhibitors of VEG F-receptor tyrosine kinase activity, the compounds of the invention may primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other "liquid tumors", especially those expressing c-kit, KDR, Flt-1 or Flt-3), such as especially breast cancer, cancer of the colon, lung cancer (especially small-cell lung cancer), cancer of the prostate or Kaposi's sarcoma. A compound of Formula IA (or exemplary formula thereof (or an N-oxide thereof inhibits the growth of tumours and is especially suited to preventing the metastatic spread of tumors and the growth of micrometastases.

One class of target kinases of the compounds of the present invention are Bcr-Abl mutants. The mutants Glu255→Lysine, Glu255→Valine or the Thr315→Isoleucine may be especially mentioned, most especially the Thr315→Isoleucine mutant.

Other Bcr-Abl mutants include Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr311→Ile, Glu459→Lys and Phe486→Ser.

The compounds of Formula IA are in particular useful to treat AML via inhibition of the tyrosine kinase domain of Flt-3. A further embodiment of the present invention is a method of treating acute myeloid leukemia (AML) which comprises administering a therapeutically effective amount of a claimed compound.

The compounds of the formula IA (or their—especially pharmaceutically acceptable—salts), due to their ability to inhibit FGFR, are especially useful in the treatment of (especially abnormal) growth, tissue repair, remodeling; cell migration, cell differentiation, skeletal and/or limb development, wound healing, signal transduction, hematopoiesis and/or angiogenesis, as well as tumorigenesis, or tumors or cancers, including metastasis and metastasis formation, especially in the treatment of human tumours, such as non small-cell lung cancers, squamous carcinoma (head and neck), breast, gastric, e.g. pancreatic adenocarcinomas ovarian, colon and/or prostate cancers as well as in and astrocytomas, gliomas, bladder cancer, epithelial cancers, e.g. of the bladder or cervix, multiple myeloma, squamous carcinoma (head and neck), such as oral squamous cell carcinoma, retinoblastoma, sarcoma, such as synovial carcinoma, and/or skin tumors; 8p11 myeloproliferative syndrome=Eosinophilic Myeloproliferative Syndrome (EMS); skeletal abnormalities, human dwarfism, including achondroplasia, craniosyneostosis syndromes and dwarfism syndromes, skeletal dysplasias including hypochondroplasia, severe achondroplasia with developmental delay, acanthosis nigracans, thanatophoric dysplasia, craniosynostosis phenotypes, e.g. Muenke coronal craniosynostosis or Crouzon syndrome with acanthosis nigricans, Pfeiffer syndrome, restrained chondrocyte maturation, bone growth inhibition; inflammatory or autoimmune diseases, such as rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and/or myasthenia gravis; Autosomal Dominant Hypophosphatemic Rickets (ADHR), X-chromosome linked hypophosphatemic rickets (XLH), tumor-induced Osteomalacia (TIO), fibrous dysplasia of the bone (FH); Chronic Obstructive Pulmonary Disease (COPD); obesity, diabetes and/or diseases related thereto, such as metabolic syndrome, cardiovascular diseases, hypertension, aberrant cholesterol and triglyceride levels, dermatological disorders (e.g. infections, varicose veins, Acanthosis nigricans, eczema, exercise intolerance, diabetes type 2, insulin resistance, hypercholesterolemia, cholelithiasis, orthopedic injury, thromboembolic disease, coronary or vascular restriction (e.g. atherosclerosis), daytime sleepiness, sleep apnoea, end stage renal disease, gallbladder disease, gout, heat disorders, impaired immune response, impaired respiratory function, infections following wounds, infertility, liver disease, lower back pain, obstetric and gynecological complications, pancreatitis, stroke, surgical complications, urinary stress incontinence and/or gastrointestinal disorders.

A method of promoting localized neochondrogenesis in a cartilage in a mammal comprising administering locally to the cartilage certain kinase inhibitors is described in WO2006/038112. Surprisingly, it was found that the compounds of formula IA as defined herein can be employed in the same manner. Hence, the present invention also relates to a method of promoting localized neochondrogenesis in a cartilage in a mammal comprising administering locally to the cartilage a urea derivatives of formula (IA) as defined above or pharmaceutically acceptable salts, hydrates, solvates, esters, N-oxides protected derivatives, individual isomers and mixture of isomers thereof or prodrugs thereof, in a quantity which is effective to promoting localized neochondrogenesis. The compound of formula IA is further useful in the treatment of osteoarthritis in the context of neochondrogenesis.

The term "treatment" includes also prophylaxis including preventative treatment, e.g. in patients where mutations or changes have been found that indicate that they are or may be prone to the development of a disease, or preferably therapeutic (including but not limited to palliative, curative, symptom-alleviating, symptom-reducing, disease- or symptom-suppressing, progression-delaying, kinase-regulating and/or kinase-inhibiting) treatment of said diseases, especially of any one or more of the diseases mentioned above.

Treatment of an animal is preferred. An animal is preferably a warm-blooded animal, more preferably a mammal. A human (which generally also falls under the general term "animal") is especially a patient or a person that (e.g. due to some mutation or other features) is prone to a risk for a disease as defined above or below.

Pharmaceutical Preparations, Methods, and Uses

The present invention relates also to pharmaceutical compositions that comprise a compound of Formula IA (or exemplary formula thereof) or a N-oxide thereof as active ingredient and that can be used especially in the treatment of the aforementioned diseases.

The pharmacologically acceptable compounds of the present invention may be used, for example, for the preparation of pharmaceutical compositions that comprise a pharmaceutically effective amount of a compound of the Formula IA (or exemplary formula thereof), or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention of (=prophylaxis against) a disease that responds to inhibition of tyrosin protein kinase activity, especially one of the diseases mentioned above as being preferred for use of a compound of Formula IA (or exemplary formula thereof), comprising an amount of a novel compound of Formula IA (or exemplary formula thereof), or a pharmaceutically acceptable salt thereof, which is effective for said inhibition, together with at least one pharmaceutically acceptable carrier.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of Formula IA (or exemplary formula thereof), a tautomer, a N-oxide or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating (especially tumor) diseases, especially those mentioned hereinabove.

The invention relates also to processes and to the use of compounds of Formula IA (or exemplary formula thereof) or N-oxides thereof for the preparation of pharmaceutical preparations which comprise compounds of Formula IA (or exemplary formula thereof) or N-oxides thereof as active component (active ingredient).

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, sprays, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity increasing agents or solubilizers, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

Injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, for example for identification purposes or to indicate different doses of active ingredient.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, and also soft, sealed capsules consisting of gelatin and a plasticizer. The hard capsules may contain the active ingredient in the form of granules, for example in admixture with fillers, binders, and/ or glidants, and optionally stabilizers. In soft capsules, the active ingredient is preferably dissolved or suspended in suitable liquid excipients, to which stabilizers and detergents may also be added.

Pharmaceutical compositions suitable for rectal administration are, for example, suppositories that consist of a combination of the active ingredient and a suppository base.

For parenteral administration, aqueous solutions of an active ingredient in water-soluble form, for example of a water-soluble salt, or aqueous injection suspensions that contain viscosity-increasing substances, for example sodium carboxymethylcellulose, sorbitbl and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

The invention relates likewise to a process or a method for the treatment of one of the diseases (pathological conditions) mentioned herein, especially a disease which responds to an inhibition of a tyrosine kinase, more especially as mentioned above, most especially FGFR, especially a corresponding neoplastic disease. The compounds of Formula IA (or exemplary formula thereof) or N-oxides thereof (this also including salts, esters or the like) can be administered as such or especially in the form of pharmaceutical compositions, prophylactically or therapeutically, preferably in an amount effective against the said diseases, to an animal, preferably to a warm-blooded animal, for example a human, each preferably requiring such treatment. In the case of an individual having a bodyweight of about 70 kg the daily dose administered is for example from approximately 0.001 g to approximately 12 g, preferably for example from approximately 0.1 g to approximately 3 g, of a compound of the present invention. "Approximately" preferably means with up to 10% deviation, more preferably with less than 1% deviation from the given number, respectively.

A disease "which responds" is one where it can be shown that some beneficial effect can be found.

The invention also provides for a method of treating a protein kinase dependent disease, comprising administering to a warm-blooded animal, for example a human, one or more cytostatic or cytotoxic compounds e.g. Glivec® in combination with a compound of the invention, whether at the same time, or a separate time. The term "the same time" is taken to mean in quick succession or immediately after one another.

The present invention relates especially also to the use of a compound of Formula IA (or exemplary formula thereof) or N-oxides thereof, or a pharmaceutically acceptable salt thereof, especially a compound of Formula IA (or exemplary formula thereof) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukaemia which responds to an inhibition of the Abl tyrosine kinase.

The preferred dose quantity, composition, and preparation of pharmaceutical formulations (medicines) which are to be used in each case are described above.

A compound of the Formula IA (or exemplary formula thereof) may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, anti-neoplastic antimetabolites, platin compounds, compounds decreasing the protein kinase activity and ATPase activity, further anti-angiogenic compounds, gonadorelin agonists, antiandrogens, bengamides, bisphosphonates, antiproliferative antibodies, temozolomide (TEMODAL®), esteroids, like dexamethasone, proteasome inhibitors, like velcade, and/or thalidomide.

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be Formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal Formulation, e.g. CAELYX™), epirubicin, idarubicin and nemorubicin, the anthraquinones mitoxantrone and losoxantrone, and the podophyllotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™: Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel; the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the Insulin-like Growth Factor I Receptor (IGF-IR) and the Cyclin-dependent kinases (CDKs), phosphatidyl inositol 3 kinase inhibitors (PI3K) and protein kinase B (PKB) inhibitors (e.g. as mentioned in WO 20051054238 and WO 2005/054237), inhibitors of heat shock protein 90 (HSP90) (an ATPase enzyme) and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958, WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin described by M. S. O'Reilly et al, Cell 79, 1994, 315-328; and Endostatin™, described by M. S. O'Reilly et al, Cell 88, 1997, 277-285; compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266, EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980; compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;
compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;
compounds which decreases the activity of the protein kinase C are especially those staurosporine derivatives disclosed in EP 0 296 110 (pharmaceutical preparation described in WO 00/48571) which compounds are protein kinase C inhibitors; further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632, KRN-633 and SU5416;
anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be Formulated, e.g. as disclosed in U.S. Pat. No. 5,843,901.

The term "anti-androgens" as used herein includes, but is not limited to bicalutamide (CASODEX™), which can be Formulated, e.g. as disclosed in U.S. Pat. No. 4,636,505.

The term "bengamides" relates to bengamides and derivatives thereof having antiproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOST™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin T, rituximab (Rituxan®), PRO64553 (anti-CD40) and 2C4 Antibody.

For the treatment of acute myeloid leukemia (AML), compounds of Formula IA (or exemplary formula thereof) can be used in combination with standard leukemia therapies, especially in combination with therapies used for the treatment of AML. In particular, compounds of formula IA (or exemplary formula thereof) can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium. "The Merck Index" or from databases, e.g. Patents International (e.g. IMS World Publications).

The above-mentioned compounds, which can be used in combination with a compound of the Formula IA (or exemplary formula thereof), can be prepared and administered as described in the art such as in the documents cited above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

Where subsequently or above the term "use" is mentioned (as verb or noun) (relating to the use of a compound of the formula IA or a (especially pharmaceutically acceptable) salt thereof), this (if not indicated differently or suggested differently by the context) includes any one or more of the following embodiments of the invention, respectively (if not stated otherwise): the use in the treatment of a protein (especially tyrosine) kinase modulation (especially inhibition) responsive disease, the use for the manufacture of pharmaceutical compositions for use in the treatment of a protein kinase modulation (especially inhibition) responsive disease, methods of use of one or more compounds of the formula IA in the treatment of a protein kinase modulation (especially inhibition) responsive and/or proliferative disease, pharmaceutical preparations comprising one or more compounds of the formula IA for the treatment of said protein kinase modulation (especially inhibition) responsive disease, and one or more compounds of the formula IA in the treatment of said protein kinase modulation (especially inhibition) responsive disease, as appropriate and expedient, if not stated otherwise. In particular, diseases to be treated and are thus preferred for "use" of a compound of formula IA are selected from (especially tyrosine) protein kinase modulation (especially inhibition) responsive (meaning also "supported", not only "dependent", including also situations where a disease is responding to modulation, especially inhibition, of a protein kinase, that is, the activity of the protein kinase supports or even causes disease manifestation) diseases mentioned above or, especially proliferative diseases mentioned above or below. Preferably, a protein kinase modulation (especially inhibition) responsive disease is one that responds to inhibition of one or more of the kinases mentioned above and below, more preferably FGFR.

Process of Manufacture

A compound of formula IA is prepared analogously to methods that, for other compounds, are in principle known in the art, so that for the novel compounds of the formula IA the process is novel as analogy process, preferably by reacting an aniline compound of the formula IIA,

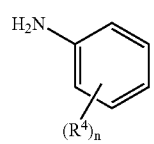

(IIA)

wherein $R^4$ and n are as defined for a compound of the formula IA, with an amine of the formula IIIA,

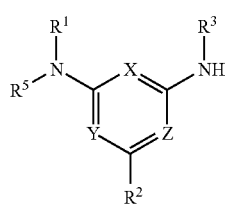

(IIIA)

wherein $R^1$, $R^2$, $R^3$, $R^5$, X, Y and Z are as defined for a compound of the formula IA, in the presence of a bisreactive carbonic acid derivative;

and, if desired, transforming a compound of formula IA into a different compound of formula IA, transforming a salt of an obtainable compound of formula IA into the free compound or a different salt, transforming an obtainable free compound of formula IA into a salt thereof, and/or separating an obtainable mixture of isomers of a compound of formula I into individual isomers.

In the reaction, the bisreactive carbonic acid derivative is preferably an anhydride of carbonic acid or more preferably a carbonic dihalogenide, especially carbonic dichloride (phosgene). The reaction can preferably take place by reacting first a compound of the formula IIA (preferred) or a compound of the formula IIIA with the bisreactive carbonic acid derivative to the corresponding isocyanate to which then the other compound (of the formula IIIA or IIA, respectively) is added. The first reaction preferably takes place in an appropriate solvent, such as an ether, e.g. dioxane, at elevated temperatures, e.g. from 20° C. to the reflux temperature of the reaction mixture, and can preferably be followed by concentration of the resulting isocyanate solution to provide the isocyanate in preferably solid or oil form. The second reaction of the isocyanate then takes place after addition of an appropriate solvent, especially N-methylpyrrolidone (NMP) and/or toluene, at elevated temperature, e.g. from 20° C. to the reflux temperature of the reaction mixture, and addition of the complementary amine of the formula IIIA or IIA, respectively.

Both reactions preferably take place under a protecting gas, especially nitrogen or argon.

Optional Reactions and Conversions

A compound of the formula IA may be converted into a different compounds of the formula I.

For example, in a compound of the formula IA wherein $R^1$ is benzyloxyphenylamino or 4-benzylpiperazin-1-yl-phenylamino, the benzyl moiety may be removed by hydrogenation, e.g. in the presence of a noble metal catalyst, such as palladium on coal, in an appropriate solvent, such as an alcohol, e.g. methanol, at appropriate temperatures, e.g. from 0 to 50° C., in the case of removal from the piperazine nitrogen in the additional presence of an acid, e.g. HCl, to yield the corresponding compound wherein instead of the benzyl moiety a hydrogen is present.

A compound of formula IA can be converted to a corresponding N-oxide. The reaction is carried out with a suitable oxidizing agent, preferably a peroxide, for example m-chloroperbenzoic acid, in a suitable solvent, e.g. halogenated hydrocarbon, typically chloroform or dichloromethane, or in a lower alkanecarboxylic acid, typically acetic acid, preferably at a temperature between 0° C. and the boiling temperature of the reaction mixture, especially at about room temperature.

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Salts of compounds of formula IA having at least one salt-forming group may be prepared in a manner known per se. For example, an acid addition salt of compounds of formula IA with basic groups (e.g. basic nitrogen) can be obtained in customary manner, e.g. by treating a compound of the formula IA with an acid or a suitable anion exchange reagent. A salt of a compound of formula IA having acid groups may be formed by treating the compound with a metal compound, such as an alkali metal salt of a suitable organic carboxylic acid, e.g. the sodium salt of 2-ethylhexanoic acid, with an organic alkali metal or alkaline earth metal compound, such as the corresponding hydroxide, carbonate or hydrogen carbonate, such as sodium or potassium hydroxide, carbonate or hydrogen carbonate, with a corresponding calcium compound or with ammonia or a suitable organic amine, stoichiometric amounts or only a small excess of the salt-forming agent preferably being used. Internal salts of compounds of formula IA containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

A salt of a compound of the formula IA (=compound of the invention) can be converted in customary manner into the free compound; a metal or ammonium salt can be converted, for example, by treatment with a suitable acid, and an acid addition salt, for example, by treatment with a suitable basic agent into a different salt. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula IA itself. Enantiomers may be separated through the formation of diastereomeric salts, for example by salt formation with an enantiomer-pure chiral acid, or by means of chromatography, for example by HPLC, using chromatographic substrates with chiral ligands. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Intermediates and final products can be worked up and/or purified according to standard methods, e.g. using chromatographic methods, distribution methods, (re-) crystallization, and the like.

Starting Materials

Starting materials and intermediates (both in each case including salts thereof), especially of the formulae IIA and IIIA, can be prepared in analogy to the methods described in the Examples, according to or in analogy to methods that are known in the art and/or they are commercially available.

Starting materials can, for example, preferably be prepared as follows:

Where in the starting materials and intermediates $R^1$, $R^2$, $R^3$, $R^4$, $R^5$, X, Y, Z and n are used, these symbols preferably have the meanings given for a compound of the formula IA, if not indicated otherwise.

A compound of the formula IIA carrying one or more halo moieties can, for example, be pre-pared by halogenation, for example with an inorganic acid halide, such as sulfuryl chloride, in an appropriate solvent, e.g. acetonitrile, dichloromethane and/or tetrahydrofurane, preferably at temperatures in the range from −40 to 25° C., of a compound corresponding to the formula IIA, wherein up to 4 other moieties $R^4$ selected from $C_1$-$C_7$-alkyl, halo-$C_1$-$C_7$-alkyl, halo and $C_1$-$C_7$-alkoxy are present and the amino group is protected, e.g. by acetyl or tert-butoxycarbonyl (introduction of the protecting groups see e.g. in the Examples or under General Process Conditions below), followed by removal of the protecting group (e.g. acetyl by treatment with an alkali metal hydroxide, such as potassium hydroxide, in an appropriate solvent, such as ethanol, at elevated temperatures, e.g. from 30° C. to the reflux temperature of the mixture, tert-butoxycarbonyl by reaction with an acid, e.g. HCl, in an appropriate solvent, e.g. dioxane, at temperatures e.g. from −20 to 30° C.).

$R^4$=$C_1$-$C_7$-alkyl, especially methyl, can be introduced by alkylating the phenyl ring (especially where already $C_1$-$C_7$-alkoxy moieties $R^4$ are present) in a corresponding precursor compound also of the formula IIA (with protection and deprotection of the amino group as in the preceding paragraph) with a $C_1$-$C_7$-alkylhalogenide (e.g. -iodide) in an appropriate solvent, e.g. tetrahydrofurane, at temperatures preferably from −50 to 25° C., after reaction of the precursor compound of the formula IIA with a strong base, e.g. butyl- or tert-butyl-lithium, in an appropriate solvent, e.g. pentane and tetrahydrofurane, at preferred temperatures in the range from −80 to 0° C.

A compound of the formula IIIA can, for example, be prepared as follows by reacting a compound of the formula VIA,

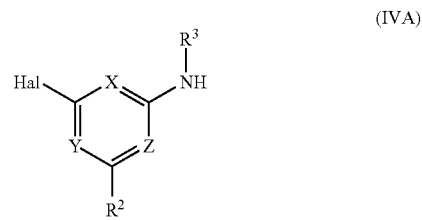

(IVA)

wherein Hal is halogen, especially chloro or bromo, with an amine of the formula VA,

(VA)

in the presence of an acid, e.g. acetic acid or hydrochloric acid, in an appropriate solvent, e.g. water or dioxane, at elevated temperatures, e.g. in the range from 50 to 160° C. (if required in a tube).

Alternatively, a compound of the formula IIIA wherein $R^1$ is phenyl substituted by [4-($C_1$-$C_7$-alkyl)-piperazin-1-yl]-carbonyl can be obtained by reacting a compound of the formula IVA as defined above with a compound of the formula VIA,

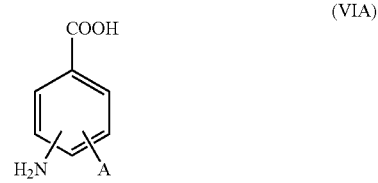

(VIA)

wherein A is hydrogen, $C_1$-$C_7$-alkoxy or halo, preferably in the presence of an acid, e.g. HCl, in an appropriate solvent, e.g. dioxane, at elevated temperatures, e.g. from 50 to 170° C. (e.g. in a microwave oven), and then reacting the resulting compound of the formula VIIA

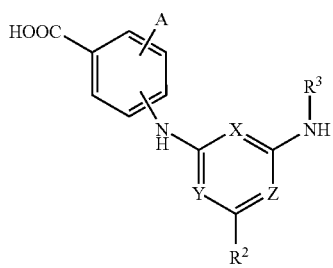

(VIIA)

wherein the moieties are as defined under formula IVA and VIA, in the presence of a coupling agent, such as propylphosphonic anhydride, in an appropriate solvent, such as DMF, in the presence of nitrogen base, e.g. triethylamine and/or 4-dimethylamino-pyridine, preferably at temperatures in the range from 0 to 50° C. to the corresponding compound of the formula IIIA.

A compound of the formula VA wherein $R^5$ is hydrogen can, for example, be obtained by reducing a corresponding compound wherein instead of the amino group ($NR^3$) a nitro group is present, e.g. with iron powder in ethanol, water and acetic acid at elevated temperatures, e.g. from 30 to 100° C., or with hydrogen in the presence of a catalyst, e.g. Raney-Ni in methanol at temperatures e.g. from 0 to 50° C. In both cases other customary solvents are possible. A corresponding compound of the formula VA wherein $R^5$ is $C_1$-$C_7$-alkyl can then be obtained by alkylation, e.g. with a corresponding $C_1$-$C_7$-alkylhalogenide.

The corresponding starting materials as well as other compounds of the formula VA can be obtained in analogy to or by the methods described in the Examples, in accordance with procedures known in the art or they are commercially available.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula IA is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminostiuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula IA described as being preferred. The invention also relates to novel intermediates and/or starting materials. Special preference is given to reaction conditions and novel intermediates that are identical or analogous to those mentioned in the Examples.

PREFERRED EMBODIMENTS ACCORDING TO THE INVENTION

In the preferred embodiments as well as in preceding and following embodiments of more general scope, also in the claims, any one or more or all general expressions or symbols, independently of each other, can be replaced by the corresponding more specific definitions provided above and below, thus yielding more preferred embodiments of the invention.

Preferred are the embodiments given in the claims which are therefore incorporated here by reference. Especially preferred is a compound of the formula IA as given in any one group A, B or C above. Very preferred are one or more compounds of the formula IA given in the Examples, as well as (especially pharmaceutically acceptable) salts thereof.

EXAMPLES

The following Examples serve to illustrate the invention without limiting the scope thereof. Temperatures are measured in degrees Celsius. Unless otherwise indicated, the reactions take place at room temperature. The $R_f$ values which indicate the ratio of the distance moved by each substance to the distance moved by the eluent front are determined on silica gel thin-layer plates 5×10 cm TLC plates, silica gel $F_{254}$ (Merck, Darmstadt, Germany) by thin-layer chromatography using the solvent systems indicated below.

Analytical HPLC Conditions:
System 1
Linear gradient 20-100% $CH_3CN$ in 5 min+1.5 min 100% $CH_3CN$ (0.1% TFA); detection at 215 nm, flow rate 1 mL/min at 30° C. Column: Nucleosil 100-3 C18 (70×4.0 mm).

Abbreviations and Acronyms:
AcOH acetic acid
API-MS atmospheric pressure ionization mass spectroscopy
brine saturated solution of NaCl in water
celite Celite® (The Celite Corporation)=filtering aid based on diatomaceous earth
$CH_3CN$ acetonitrile
DCM dichloromethane
conc. concentrated
DIEA diisopropylethylamine
DMAP 4-dimethylamino-pyridine
DMF dimethyl formamide
DMP 1,3-dimethyl-3,4,5,6-tetrahydro-2-(1H)-pyrimidinone
DMSO dimethylsulfoxide
equiv equivalent(s)
ESI-MS electrospray ionization mass spectroscopy
$Et_2O$ diethyl ether
$Et_3N$ triethylamine
EtOAc ethyl acetate
EtOH ethanol
$HNO_3$ nitric acid
$H_2SO_4$ sulphuric acid
h hour(s)
Hex hexane
HCl hydrochloric acid
$H_2O$ water
HPLC high pressure liquid chromatography
L liter(s)
LiOH lithium hydroxide
Me methyl
MeOH methanol
mL milliliter(s)
min minute(s)
m.p. melting point
MPLC medium pressure liquid chromatography
MS mass spectrum
NaH sodium hydride
$Na_2CO_3$ sodium carbonate
$NaHCO_3$ sodium bicarbonate
$Na_2SO_4$ sodium sulfate
$NH_3^{aq}$ aqueous ammonia
NMP 1-methyl-2-pyrrolidone
NMR Nuclear Magnetic Resonance
$PdCl_2(dppf)$ [1,1'-bis(diphenylphosphino)ferrocene]dichloropalladium(II)
$Pd(PPh_3)_4$ tetrakis(triphenylphosphine)palladium(0)
$Pd(PhCN)_2Cl_2$ Bis(benzonitrile)palladium (II) chloride
Ph phenyl
$R_f$ ratio of fronts (TLC)
RT room temperature
TBTU O-(Benzotriazol-1-yl)-N,N,N',N'-tetramethyluronium tetrafluoroborate
TFA $CF_3COOH$ (trifluoroacetic acid)
THF tetrahydrofuran
TLC thin layer chromatography
$T_R$ retention time
wt. weight
Microwave Apparatus: Emrys Optimizer (Biotage)
Example for Reaction Scheme

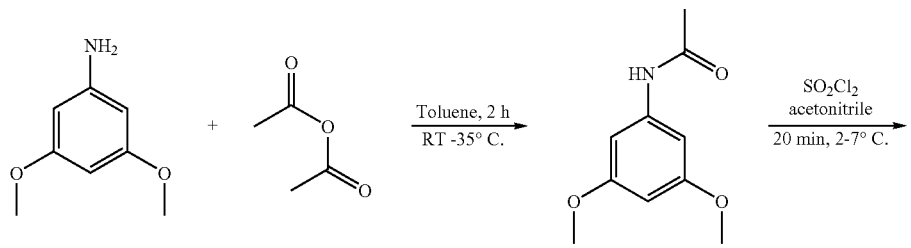

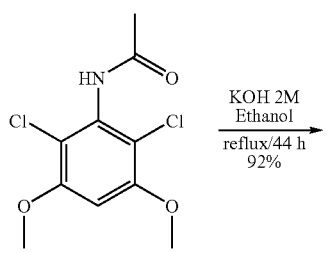

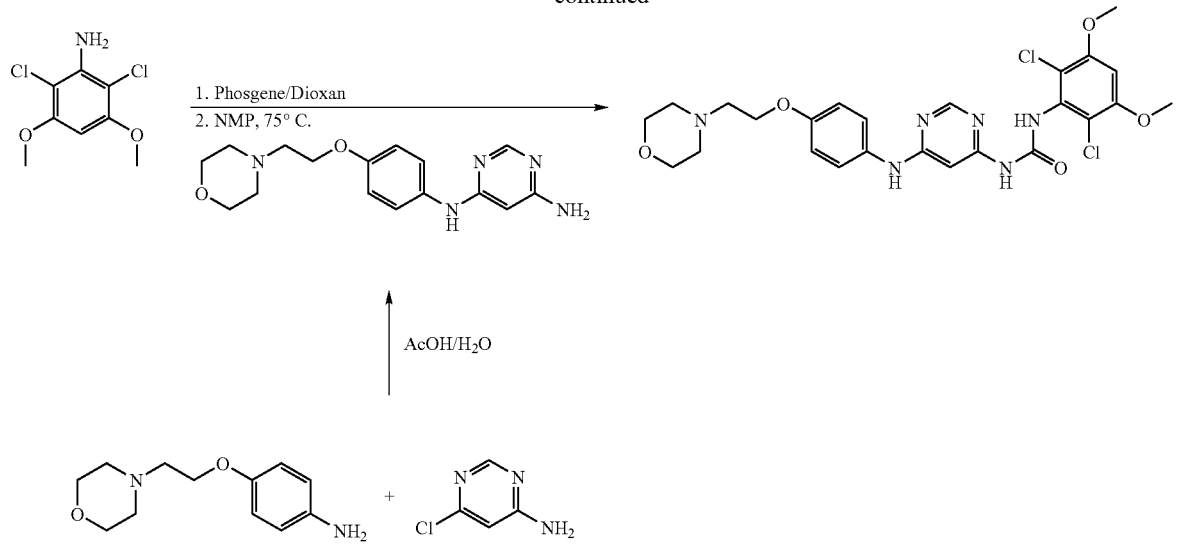

Example 1

1-(2,6-Dichloro-3,5-dimethoxy-phenyl)-3-{6-[4-(2-morpholin-4-yl-ethoxy)phenylamino]-pyrimidin-4-yl}-urea Phosgene (20% in toluene, 0.8 mL, 1.58 mmol, 2.4 equiv) is added to a solution of 2,6-dichloro-3,5-dimethoxyaniline (175 mg, 0.79 mmol, 1.2 equiv) in dioxane (2.5 mL), under an argon atmosphere. The mixture is heated to reflux, stirred for 1 h, allowed to cool to RT, and concentrated in vacuo. The resulting isocyanate is added to a solution of N-[4-(2-morpholin-4-yl-ethoxy)-phenyl]-pyrimidine-4,6-diamine (208.5 mg, 0.66 mmol) in NMP (2 mL), at 75° C. and under an argon atmosphere. The reaction mixture is stirred at 75° C. for 2 h, allowed to cool to RT, and is then diluted with DCM and a saturated aqueous solution of $NaHCO_3$. The aqueous layer is separated and extracted with DCM. The organic phase is washed with brine, dried ($Na_2SO_4$), filtered and concentrated. Purification of the crude product by silica gel column chromatography (DCM/MeOH+1% $NH_3^{aq}$, 96:4), followed by trituration of the resulting material in MeOH, affords the title compound as a white solid: ESI-MS: 562.9/564.9 $[MH]^+$; $t_R$=2.99 min (purity: 100%, system 1); TLC: $R_f$=0.36 (DCM/MeOH+1% $NH_3^{aq}$, 93:7).

Step 1.1: N-[4-(2-Morpholin-4-yl-ethoxy)-phenyl]-pyrimidine-46-diamine

A mixture of 6-chloro-pyrimidin-4-ylamine (194 mg, 1.5 mmol, 1.3 equiv), 4-(2-morpholin-4-yl-ethoxy)-phenylamine (256 mg, 1.15 mmol) in $H_2O$ (1 mL) and glacial acetic acid (5 mL) is stirred for 16 h at 100° C. After solvent evaporation, the residue is taken up in DCM and diluted with a saturated aqueous solution of $NaHCO_3$. The aqueous layer is separated and extracted with DCM. The organic phase is washed with brine, dried ($Na_2SO_4$), filtered and concentrated. The residue is triturated in EtOAc to provide the title compound as a grey solid: ESI-MS: 316.2 $[MH]^+$; $t_R$=1.00 min (purity: 95%, system 1); TLC: $R_f$=0.22 (DCM/MeOH+1% $NH_3^{aq}$, 93:7).

Step 1.2: 4-(2-Morpholin-4-yl-ethoxy)-phenylamine 4-(2-Chloro-ethyl)-morpholine hydrochloride (4.2 g, 22 mmol, 1.2 equiv) is added in one portion to a mixture of 4-aminophenol (2 g, 18.3 mmol) and finely powdered sodium hydroxide (1.87 g, 45.8 mmol, 2.5 equiv) in DMF (32 mL), under an argon atmosphere. The reaction mixture is stirred for 23.5 h at RT. The resulting dark suspension is filtered. The filtrate is diluted with DCM (200 ml) and washed with brine (2×60 mL). The organic phase is dried (sodium sulfate), filtered and concentrated. Purification of the residue by silica gel column chromatography (DCM/EtOH, 95:5→7:3) provides the title compound as a yellow-brown solid: API-MS: 223.2 $[MH]^+$; TLC: $R_f$=0.31 (DCM/EtOH, 9:1).

Step 1.3: 2,6-Dichloro-3,5-dimethoxyaniline

To a solution of N-(2,6-dichloro-3,5-dimethoxy-phenyl)-acetamide (34.5 g, 264 mmol) in ethanol (1.3 L), 2M KOH (0.72 L) is added. Then, the reaction mixture is heated to reflux, stirred for 44 h at reflux, then allowed to cool to RT. The resulting suspension is cooled to 0° C. stirred for 1 h, and filtered. The residue is washed with a small portion of cold EtOH/$H_2O$ (1:1) and with cold $H_2O$ till neutrality, and dried to provide the title compound as a white solid: ESI-MS: 222.0/224.0 $[MH]^+$, TLC: $R_f$=0.52 (Hex/EtOAc, 1:1).

Step 1.4: N-(2,6-Dichloro-3,5-dimethoxy-phenyl)-acetamide

Sulfurylchloride (26.9 ml, 325 mmol, 1.93 equiv) is added (in 7 min) to a cold (0° C.) suspension of N-(3,5-dimethoxyphenyl)-acetamide (32.9 g, 169 mmol) in $CH_3CN$ (500 mL), under an argon atmosphere. The resulting yellowish mixture is allowed to stir for 30 min and quenched by dropwise addition of a saturated aqueous solution of sodium bicarbonate (250 mL). The resulting precipitate is collected by vacuum filtration, washed with $H_2O$ (300 ml) and dried to afford 20 g of the desired product (batch 1). The filtrate is diluted with a saturated aqueous solution of $NaHCO_3$ (300 mL) and extracted with EtOAc (2×300 mL). The organic phase is washed with $H_2O$ and brine, dried ($Na_2SO_4$), filtered and concentrated. The residue is purified by silica gel column chromatography (EtOAc/Hex, 1:1→2:1) to provide 8.8 g of product (batch 2). Batch 1 and 2 are combined and stirred in hexane. The solid is collected by filtration, washed with hexane and dried to afford the title compound as a white solid. ESI-MS: 264.0/266.0 [MH]$^+$, TLC: R$_f$=0.15 (Hex/EtOAc, 1:1).

Step 1.5: N-(3,5-Dimethoxy-phenyl)-acetamide

Acetic anhydride (13 ml, 137 mmol, 1.05 equiv) is added (in 15 min) to a suspension of 3,5-dimethoxyaniline (20 g, 131 mmol) in toluene (110 mL), keeping the internal temperature in the range of 35-45° C. The reaction mixture is allowed to stir for 20 h at RT. The resulting thick, grey suspension is diluted with hexane (55 mL) and filtered. The residue in the filter is washed with toluene/Hex (2:1, 70 mL) and Hex, and dried to provide the title compound as a white solid. API-ES-MS: 196.1 [MH]$^+$, t$_R$=3.03 min (purity: 100%, system 1).

Example 2

3-(2,6-Dichloro-3,5-dimethoxy-phenyl)-1-methyl-1-{6-[3-(4-methyl-piperazin-1-ylmethyl)-phenylamino]-pyrimidin-4-yl}-urea Phosgene (20% in toluene, 1 mL, 2.0 mmol, 2.4 equiv) is added to a solution of 2,6-dichloro-3,5-dimethoxyaniline (221 mg, 1.0 mmol, 1.2 equiv) in dioxane (2.5 mL), under an argon atmosphere. The mixture is heated to reflux, stirred for 1 h, allowed to cool to RT, and concentrated in vacuo. The resulting isocyanate is added to a solution of N-methyl-N'-[3-(4-methyl-piperazin-1-ylmethyl)-phenyl]-pyrimidine-4,6-diamine (Step 2.1) (259 mg, 0.83 mmol) in toluene (5 mL), at reflux and under an argon atmosphere. The reaction mixture is stirred at reflux for 3 h, allowed to cool to RT, and diluted with DCM and a saturated aqueous solution of NaHCO$_3$. The aqueous layer is separated and extracted with DCM. The organic phase is washed with brine, dried (Na$_2$SO$_4$), filtered and concentrated. Purification of the crude product by silica gel column chromatography (DCM/MeOH+1% NH$_3{}^{aq}$, 95:5) affords the title compound as a yellow solid: ESI-MS: 560.0/562.0 [MH]$^+$; t$_R$=3.26 min (purity: 99%, system 1); TLC: R$_f$=0.37 (DCM/MeOH+1% NH$_3{}^{aq}$, 9:1).

Step 2.1: N-Methyl-N'-[3-(4-methyl-piperazin-1-Ylmethyl)-phenyl]-pyrimidine-4,6-diamine A mixture of (6-chloro-pyrimidin-4-yl)-methyl-amine (385 mg, 2.68 mmol, 1.1 equiv), 3-(4-methyl-piperazin-1-ylmethyl)-phenylamine (500 mg, 2.44 mmol) and 4N HCl in dioxane (7 mL) is heated in a sealed tube to 150° C. for 17.5 h. The solvent is removed and the residue diluted with DCM and a saturated aqueous solution of NaHCO$_3$. The aqueous layer is separated and extracted with DCM and DCM/MeOH (95:5). The organic phase is washed with brine, dried (Na$_2$SO$_4$), filtered and concentrated. Purification of the residue by silica gel MPLC (DCM/MeOH+1% NH$_3{}^{aq}$, 95:5) affords the title compound as a beige solid: ESI-MS: 313.2 [MH]$^+$; t$_R$=1.00 min (purity: 100%, system 1); TLC: R$_f$=0.05 (DCM/MeOH+1% NH$_3{}^{aq}$, 9:1).

Step 2.2: 3-(4-Methyl-piperazin-1-ylmethyl)-phenylamine

A suspension of 1-methyl-4-(3-nitro-benzyl)-piperazine (6.9 g, 29.14 mmol) and Raney Nickel (2 g) in MeOH (150 mL) is stirred for 5 h at RT, under a hydrogen atmosphere. The reaction mixture is filtered through a pad of celite and concentrated to afford the title compound as a yellow solid: ESI-MS: 206.1 [MH]$^+$.

Step 2.3: 1-Methyl-4-(3-nitro-benzyl)-piperazine

A mixture of 3-nitrobenzylchloride (5 g, 29.14 mmol), N-methylpiperazine (3.9 mL, 34.97 mmol, 1.2 equiv), potassium carbonate (8 g, 58.28, 2 equiv), and acetone (100 ml) is stirred for 15 h at reflux. The reaction mixture is allowed to cool to RT, filtered and concentrated. The residue is purified by silica gel MPLC (DCM/MeOH+1% NH$_3{}^{aq}$, 95:5) to afford the title compound as a brow oil: ESI-MS: 236.0 [MH]$^+$; t$_R$=1.40 min (purity: 100%, system 1); TLC: R$_f$=0.31 (DCM/MeOH+1% NH$_3{}^{aq}$, 9:1).

Example 3

3-(2,6-Dichloro-3,5-dimethoxy-phenyl)-1-{6-[3-(4-ethyl-piperazin-1-yl)-phenylamino]-pyrimidin-4-yl}-1-methyl-urea The title compound is prepared in analogy to the procedure described in Example 2: ESI-MS: 559.9/561.9 [MH]$^+$; t$_R$=3.75 min (purity: 100%, system 1); TLC: R$_f$=0.37 (DCM/MeOH+1% NH$_3{}^{aq}$, 92:8).

Step 3.1: N-[3-(4-Ethyl-piperazin-1-yl)-phenyl]-N'-methyl-pyrimidine-4,6-diamine The title compound is prepared in analogy to the procedure described in Step 2.1: ESI-MS: 313.2 [MH]$^+$; t$_R$=1.20 min (purity: 100%, system 1); TLC: R$_f$=0.10 (DCM/MeOH+1% NH$_3{}^{aq}$, 9:1).

Step 3.2: 3-(4-Ethyl-piperazin-1-yl)-phenylamine

The title compound is prepared in analogy to the procedure described in Step 2.2: API-MS: 206.2 [MH]$^+$; TLC: R$_f$=0.31 (DCM/EtOH, 9:1).

Step 3.3: 1-Ethyl-4-(3-nitro-phenyl)-piperazine

A mixture of 1-fluoro-3-nitrobenzene (3.2 mL, 29.7 mmol) and N-ethyl-piperazine (7.6 mL, 59.4 mmol, 2 equiv) is heated to reflux and stirred for 117 h. The reaction mixture is allowed to cool to RT and diluted with H$_2$O (40 mL) and DCM/MeOH (9:1, 80 mL). The aqueous layer is separated and extracted with DCM/MeOH (9:1). The organic phase is washed with brine, dried (Na$_2$SO$_4$), filtered and concentrated. Purification of the crude product by silica gel column chromatography (DCM/MeOH, 1:0-95:5) affords the title compound as a brown oil: ESI-MS: 236.0 [MH]$^+$; t$_R$=2.49 min (purity: 99%, system 1); TLC: R$_f$=0.26 (DCM/MeOH, 95:5).

Example 4

3-(2,6-Dichloro-3,5-dimethoxy-phenyl)-1-methyl-1-{6-[4-(2-morpholin-4-ylethoxy)-phenylamino]-pyrimidin-4-yl}-urea The title compound is prepared in analogy to the procedure described in Example 1: ESI-MS: 577.0/579.0 [MH]$^+$; t$_R$=3.53 min (purity: 95%, system 1); TLC: R$_f$=0.40 (DCM/MeOH+1% NH$_3{}^{aq}$, 93:7).

Step 4.1: N-Methyl-N'-[4-(2-morpholin-4-yl-ethoxy)-phenyl]-pyrimidine-4,6-diamine The title compound is prepared in analogy to the procedure described in Step 1.1: ESI-MS: 330.2 [MH]$^+$; $t_R$=1.10 min (purity: 100%, system 1); TLC: $R_f$=0.16 (DCM/MeOH+1% NH$_3^{aq}$, 93:7).

Example 5

1-[6-(4-Benzyloxy-phenylamino)-pyrimidin-4-yl]-3-(2,6-dichloro-3,5-dimethoxyphenyl)-1-methyl-urea The title compound is prepared in analogy to the procedure described in Example 2: ESI-MS: 553.9/555.9 [MH]$^+$; $t_R$=5.16 min (purity: 100%, system 1).

Step 5.1: N-(4-Benzyloxy-phenyl)-N'-methyl-pyrimidine-4,6-diamine

The title compound is prepared in analogy to the procedure described in Step 1.1: ESI-MS: 307.2 [MH]$^+$; $t_R$=3.72 min (purity: 100%, system 1).

Example 6

3-(2,6-Dichloro-3,5-dimethoxy-phenyl)-1-[6-(4-hydroxy-phenylamino)-pyrimidin-4-yl]-1-methyl-urea A suspension of 1-[6-(4-benzyloxy-phenylamino)-pyrimidin-4-yl]-3-(2,6-dichloro-3,5-dimethoxy-phenyl)-1-methyl-urea (Example 5) (67 mg, 0.121 mmol), palladium on carbon (20 mg), and MeOH (3.5 mL) is stirred for 3 h at RT, under a hydrogen atmosphere. The reaction mixture is filtered through a pad of celite and concentrated. The residue is purified by silica gel column chromatography to provide the title compound as a brown solid: ESI-MS: 464.2/466.2 [MH]$^+$; $t_R$=3.91 min (purity: 100%, system 1).

Example 7

1-(2-Chloro-3,5-dimethoxy-6-methyl-phenyl)$_{3-36}$-[4-(4-ethyl-piperazin-1-yl)phenylamino]-pyrimidin-4-yl-urea The title compound is prepared in analogy to the procedure described in Example 2: ESI-MS: 526.1/528.1 [MH]; $t_R$=3.12 min (purity: 100%, system 1); TLC: $R_f$=0.13 (DCM/MeOH+1% NH$_3^{aq}$, 93:7).

Step 7.1: N-[4-(4-Ethyl-piperazin-1-yl)-phenyl]-pyrimidine-4,6-diamine

The title compound is prepared in analogy to the procedure described in Step 1.1: ESI-MS: 299.1 [MH]$^+$; $t_R$=1.00 min (purity: >95%, system 1).

Step 7.2: 4-(4-Ethylpiperazin-1-yl)-aniline

A suspension of 1-ethyl-4-(4-nitro-phenyl)-piperazine (6.2 g, 26.35 mmol) and Raney Nickel (2 g) in MeOH (120 mL) is stirred for 7 h at RT, under a hydrogen atmosphere. The reaction mixture is filtered through a pad of celite and concentrated to afford the title compound as a violet solid: ESI-MS: 206.1 [MH]$^+$; TLC: $R_f$=0.15 (DCM/MeOH+1% NH$_3^{aq}$, 9:1).

Step 7.3: 1-Ethyl-4-(4-nitro-phenyl)-piperazine

A mixture of 1-bromo-4-nitrobenzene (6 g, 29.7 mmol) and 1-ethylpiperazine (7.6 mL, 59.4 mmol, 2 equiv) is heated to 80° C. for 15 h. After cooling to RT, the reaction mixture is diluted with water and DCM/MeOH, 9:1. The aqueous layer is separated and extracted with DCM/MeOH, 9:1. The organic phase is washed with brine, dried (sodium sulfate), filtered and concentrated. Purification of the residue by silica gel column chromatography (DCM/MeOH+1% NH$_3^{aq}$, 9:1) affords the title compound as a yellow solid: ESI-MS: 236.0 [MH]$^+$; $t_R$=2.35 min (purity: 100%, system 1); TLC: $R_f$=0.50 (DCM/MeOH+1% NH$_3^{aq}$, 9:1).

Step 7.4: 2-Chloro-3,5-dimethoxy-6-methyl-phenyl-amine

HCl (91 mL, 360 mmol, 8 equiv, 4N in dioxane) is added dropwise to a cooled (10° C.) solution of (2-chloro-3,5-dimethoxy-6-methyl-phenyl)-carbamic acid tert-butyl ester (13.8 g, 45.7 mmol) in dioxane (150 mL), under an argon atmosphere. The reaction mixture is allowed to warm to RT, stirred for 24 h and concentrated. The residue is diluted with EtOAc, washed with a saturated aqueous solution of NaHCO$_3$, and brine, dried (Na$_2$SO$_4$), filtered and concentrated. The residue is purified by crystallization from DCM/Hex to afford the title compound. ESI-MS: 202.0 [MH]$^+$, TLC: $R_f$=0.37 (DCM).

Step 7.5: (2-Chloro-3,5-dimethoxy-6-methyl-phenyl)-carbamic acid tert-butyl ester A solution of sulfurylchloride (6.7 ml, 79.8 mmol, 1.05 equiv) in DCM (140 mL) is added dropwise (75 min) to a cold (−15° C.) solution of (3,5-dimethoxy-2-methyl-phenyl)-carbamic acid tert-butyl ester (20.4 g, 76.3 mmol) in THF (330 ml), under an argon atmosphere. The reaction mixture is allowed to stir for 3 h at −15° C. and then poured onto a mixture of ice/H$_2$O (400 mL), a saturated aqueous solution of NaHCO$_3$ (400 ml), and EtOAc (400 mL). The layers are separated and the aqueous phase is extracted with EtOAc (2×200 mL). The combined organic phase is washed with H$_2$O (3×200 mL) and brine (200 mL), dried (Na$_2$SO$_4$), filtered and concentrated. The residue is purified by trituration in diethyl ether followed by silica gel column chromatography (Hex/acetone, 95:5) to afford the title compound. ESI-MS: 302.2 [MH]$^+$, TLC: $R_f$=0.13 (Hex/acetone, 9-1).

Step 7.6: (3,5-Dimethoxy-2-methyl-phenyl)-carbamic acid tert-butyl ester

A solution of tert-butyllithium (200 mL, 340 mmol, 2.4 equiv, 1.7M in pentane) is added dropwise to a cold (−65° C.) solution of (3,5-dimethoxy-phenyl)-carbamic acid tert-butyl ester (36.1 g, 142 mmol) in THF (250 mL), under an argon atmosphere. The mixture is stirred for 15 min at −65° C. and then allowed to warm to −25° C. A solution of methyliodide (10.7 mL, 171 mmol, 1.2 equiv) in THF (140 mL) is then added. The reaction mixture is allowed to stir for 1 h at −25° C. and then poured onto a mixture of ice/H$_2$O (300 mL) and EtOAc (300 mL). The layers are separated and the aqueous phase is extracted with EtOAc (2×150 mL). The combined organic phase is washed with H$_2$O (3×150 mL) and brine (200 mL), dried (Na$_2$SO$_4$), filtered and concentrated. The residue is purified by silica gel column chromatography (Hex/acetone, 95:5-9:1, 4:1) to provide the title compound. ESI-MS: 268.1 [MH]⁺, TLC: $R_f$=0.25 (Hex/acetone, 9:1).

Step 7.7: (3,5-Dimethoxy-phenyl)-carbamic acid tert-butyl ester

A solution of di-tert-butyl-dicarbonate (145 g, 651 mmol, 1.3 equiv) in THF (200 mL) is added dropwise to a solution of 3,5-dimethoxyaniline (78.2 g, 500 mmol) in THF (1.5 L) at RT, under an argon atmosphere. The reaction mixture is heated to reflux for 4.5 h (upon heating considerable gas evolution is observed), allowed to cool to RT and concentrated. The residue is diluted with EtOAc (800 mL) and H₂O (800 mL). The layers are separated and the aqueous phase is extracted with EtOAc (2×200 mL). The combined organic phase is washed with 0.1N HCl (200 mL), H₂O, and brine, dried (Na₂SO₄), filtered and concentrated. The residue is crystallized from DCM/Hex to provide the title compound. ESI-MS: 252.1 [M-H]⁻, TLC: $R_f$=0.34 (Hex/EtOAc, 3:1).

Example 8

3-(2-Chloro-3,5-dimethoxy-6-methyl-phenyl)-1-{6-[4-(4-ethyl-piperazin-1-yl)phenylamino]-pyrimidin-4-yl}-1-methyl-urea The title compound is prepared in analogy to the procedure described in Example 1: ESI-MS: 540.1/542.1 [MH]⁺; $t_R$=3.56 min (purity: 100%, system 1); TLC: $R_f$=0.13 (DCM/MeOH+1% NH₃$^{aq}$, 93:7).

Example 9

3-(2-Chloro-3,5-dimethoxy-6-methyl-phenyl)-1-{6-[4-(2-dimethylamino-ethoxy)phenylamino]-pyrimidin-4-yl}-1-methyl-urea The title compound is prepared in analogy to the procedure described in Example 1: ESI-MS: 515.2/517.2 [MH]⁺; $t_R$=3.47 min (purity: >95%, system 1).

Step 9.1: N-[4-(2-Dimethylamino-ethoxy)-phenyl]-N'-methyl-pyrimidine-4,6-diamine The title compound is prepared in analogy to the procedure described in Step 1.1: ESI-MS: 288.2 [MH]⁺; $t_R$=0.95 min (purity: 95%, system 1).

Step 9.2: 4-(2-Dimethylamino-ethoxy)-phenylamine

The title compound is prepared in analogy to the procedure described in Step 1.2: ESI-MS: 181.2 [MH]⁺; TLC: $R_f$=0.18 (DCM/MeOH, 7:3).

Example 10

3-(2-Chloro-3,5-dimethoxy-6-methyl-phenyl)-1-methyl-(6-{4-[2-(4-methylpiperazin-1-yl)-ethoxy]-phenylamino}-pyrimidin-4-yl)-urea The title compound is prepared in analogy to the procedure described in Example 2: ESI-MS: 570.0 [MH]⁺; $t_R$=3.20 min (purity: 90%, system 1), TLC: $R_f$=0.13 (DCM/MeOH+1% NH₃$^{aq}$, 93:7).

Step 10.1: N-Methyl-N'-{4-[2-(4-methyl-piperazin-1-yl)-ethoxy]-phenyl}-pyrimidine-4,6-diamine The title compound is prepared in analogy to the procedure described in Step 1.1: ESI-MS: 343.2 [MH]⁺; $t_R$=1.00 min (purity: 95%, system 1), TLC: $R_f$=0.23 (DCM/MeOH+1% NH₃$^{aq}$, 9:1).

Example 11

3-(2-Chloro-6-iodo-3,5-dimethoxy-phenyl)-1-{6-[4-(4-ethyl piperazin-1-yl)phenylamino]-pyrimidin-4-yl}-1-methyl-urea The title compound is prepared in analogy to the procedure described in Example 1: ESI-MS: 651.8/653.7 [MH]⁺; $t_R$=3.20 min (purity: 95%, system 1), TLC: $R_f$=0.18 (DCM/MeOH+1% NH₃$^{aq}$, 93:7).

Step 11.1 N-[4-(4-Ethyl-piperazin-1-yl)-phenyl]-N'-methyl-pyrimidine-4,6-diamine The title compound is prepared in analogy to the procedure described in Step 1.1: ESI-MS: 313.2 [MH]⁺; $t_R$=1.10 min (system 1): TLC: $R_f$=0.21 (DCM/MeOH, 93:7).

Step 11.2: 2-Chloro-6-iodo-3,5-dimethoxy-phenyl-amine

HCl (6.46 mL, 26 mmol, 9.1 equiv, 4N in dioxane) is added to a cooled (10° C.) solution of (2-chloro-3,5-dimethoxy-6-methyl-phenyl)-carbamic acid tert-butyl ester (1.28 g, 2.85 mmol, 92% purity) in dioxane (10 mL), under an argon atmosphere. The reaction mixture is allowed to warm to RT and then stirred for 1.5 h. The residue is diluted with EtOAc and ice/water, and made basic by addition of a saturated aqueous solution of NaHCO₃. The layers are separated. The aqueous layer is extracted with EtOAc. The organic phase is washed with brine, dried (Na₂SO₄), filtered and concentrated. The residue is purified by silica gel column chromatography (DCM) to afford the title compound. API-ES-MS: 314.0 [MH]⁺, TLC: $R_f$=0.53 (DCM).

Step 11.3: (2-Chloro-6-iodo-3,5-dimethoxy-phenyl)-carbamic acid tert-butyl ester A solution of sulfurylchloride (0.92 ml, 11.0 mmol, 1.16 equiv) in DCM (20 mL) is added dropwise (30 min) to a cold (−15° C.) solution of (2-iodo-3,5-dimethoxy-phenyl)-carbamic acid tert-butyl ester (3.6 g, 9.49 mmol) in THF (48 ml), under an argon atmosphere. The reaction mixture is allowed to stir for 1 h at −15° C. and then poured onto a mixture of ice/H₂O (100 mL), a saturated aqueous solution of NaHCO₃ (80 ml), and EtOAc (100 mL). The layers are separated and the aqueous phase is extracted with EtOAc (2×100 mL). The combined organic phase is washed with H₂O (3×60 mL) and brine (60 mL), dried (Na₂SO₄), filtered and concentrated. The residue is purified by silica gel column chromatography (DCM) followed by crystallization from DCM/Hex to afford the title compound. ESI-MS: 411.9, 413.9 [M-H]⁻, TLC: $R_f$=0.18 (DCM/Hex, 7:3).

Step 11.4: (2-Iodo-3,5-dimethoxy-phenyl)-carbamic acid tert-butyl ester

A solution of tert-butyllithium (14.1 mL, 24 mmol, 2.4 equiv, 1.7M in pentane) is added dropwise (15 min) to a cold (−65° C.) solution of (3,5-dimethoxy-phenyl)-carbamic acid tert-butyl ester. (2.53 g, 10 mmol) in THF (18 mL), under an argon atmosphere. The mixture is stirred for 15 min at −65° C. and then allowed to warm to −25° C. An excess of trifluoromethyliodide is bubbled into the yellow reaction mixture. The resulting dark mixture is poured onto a mixture of ice/$H_2O$ (60 mL) and EtOAc (60 mL). The layers are separated and the aqueous phase is extracted with EtOAc (2×30 mL). The combined organic phase is washed with $H_2O$ (3×40 mL), and brine (60 mL), dried ($Na_2SO_4$), filtered and concentrated. The residue is purified by silica gel column chromatography (DCM/Hex, 2:1) to provide the title compound. ESI-MS: 380.1 $[MH]^+$, TLC: $R_f$=0.27 (DCM/Hex, 2:1).

Step 11.5: (3,5-Dimethoxy-phenyl)-carbamic acid tert-butyl ester

A solution of di-tert.-butyl-dicarbonate (69.5 g, 312 mmol, 1.3 equiv) in THF (100 mL) is added to a solution of 3,5-dimethoxyaniline (37.5 g, 240 mmol) in THF (600 mL). The reaction mixture is heated to reflux for 3 h, allowed to cool to RT, stirred overnight, and concentrated. The residue is partitioned between EtOAc (500 mL) and $H_2O$ (500 mL). The layers are separated and the aqueous phase is extracted with EtOAc (2×100 mL). The combined organic phase is washed with 0.1N HCl (2×100 mL), $H_2O$ and brine, dried ($Na_2SO_4$), filtered and concentrated. The residue is purified by trituration with hexane to afford the title compound. ESI-MS: 254.1 $[MH]^+$, TLC: $R_f$=0.42 (Hex/EtOAc, 3:1).

Example 12

3-(2-Chloro-3,5-dimethoxy-6-methyl-phenyl)-1-{6-[4-(4-isopropyl-piperazin-1-yl)phenylamino]-pyrimidin-4-yl}-1-methyl-urea The title compound is prepared in analogy to the procedure described in Example 1: ESI-MS: 554.0/555.0 $[MH]^+$; $t_R$=3.49 min (purity: >95%, system 1), TLC: $R_f$=0.13 (DCM/MeOH+1% $NH_3^{aq}$, 93:7).

Step 12.1: N-[4-(4-Isopropyl-piperazin-1-yl)-phenyl]-N'-methyl-pyrimidine-4,6-diamine The title compound is prepared in analogy to the procedure described in Step 1.1: ESI-MS: 288.2 $[MH]^+$; $t_R$=0.95 min (purity: 95%, system 1).

Step 12.2: 4-(4-Isopropylpiperazin-1-yl)-aniline

A suspension of 1-isopropyl-4-(4-nitro-phenyl)-piperazine (5.18 g, 20.80 mmol) and 5% palladium on carbon (0.5 g) in MeOH (100 mL) is stirred for 2.7 h at RT, under a hydrogen atmosphere. The reaction mixture is filtered through a pad of celite and concentrated to afford the title compound as a violet solid: ESI-MS: 220.1 $[MH]^+$; $t_R$=0.95 min (system 1).

Step 12.3: 1-Isopropyl-4-(4-nitro-phenyl)-piperazine

A mixture of 1-bromo-4-nitrobenzene (6 g, 29.7 mmol) and 1-ethylpiperazine (7.6 ml, 59.4 mmol, 2 equiv) is heated to 80° C. for 15 h. After cooling to RT, the reaction mixture is concentrated. Purification of the residue by silica gel column chromatography (DCM/MeOH 95:5) affords the title compound as a yellow solid: ESI-MS: 250.1 $[MH]^+$; $t_R$=2.57 min (purity: 100%, system 1); TLC: $R_f$=0.16 (DCM/MeOH, 95:5).

Example 13

1-{6-[4-(4-Benzyl-piperazin-1-yl)-phenylamino]-pyrimidin-4-yl}-3-(2,6-dichloro-3,5-dimethoxy-phenyl)-1-methyl-urea The title compound is prepared in analogy to the procedure described in Example 2: ESI-MS: 621.9/623.9 $[MH]^+$; $t_R$=4.04 min (purity: 100%, system 1).

Step 13.1: N-[4-(4-Benzyl-piperazin-1-yl)-phenyl]-N'-methyl-pyrimidine-4,6-diamine The title compound is prepared in analogy to the procedure described in Step 1.1: ESI-MS: 375.1 $[MH]^+$; $t_R$=2.36 min (purity: 95%, system 1).

Step 13.2: 4-(4-Benzyl-piperazin-1-yl)-phenylamine

Iron powder (5.4 g, 97 mmol, 4 equiv) is added portionwise to an 80° C. mixture of 1-benzyl-4-(4-nitro-phenyl)-piperazine (7.2 g, 24.2 mmol), EtOH (150 mL), $H_2O$ (40 mL), and AcOH (20 mL). The reaction mixture is stirred for 1.75 h at 80° C., allowed to cool to RT, and concentrated. The residue is diluted with EtOAc and an aqueous saturated solution of $Na_2CO_3$. The layers are separated and the aqueous phase is extracted with EtOAc. The combined organic phase is washed with brine, dried ($Na_2SO_4$), filtered and concentrated to afford the title compound: ES-MS: 268.3 $[MH]^+$; single peak at $t_R$=1.30 min (system 1).

Step 13.3: 1-Benzyl-4-(4-nitro-phenyl)-piperazine

A mixture of 1-bromo-4-nitrobenzene (5 g, 24.8 mmol) and 1-benzylpiperazine (8.6 ml, 49.5 mmol, 2 equiv) is heated to 80° C. for 17 h. The reaction mixture is allowed to cool to RT, and is diluted with DCM/$H_2O$. The layers are separated and the aqueous phase is extracted with DCM. The combined organic phase is washed with brine, dried ($Na_2SO_4$), filtered and concentrated. Purification of the residue by silica gel column chromatography (Hex/EtOAc, 1:1) affords the title compound as a yellow solid: ESI-MS: 298.3 $[MH]^+$; $t_R$=3.25 min (purity: 100%, system 1).

Example 14

3-(2,6-Dichloro-3,5-dimethoxy-phenyl)-1-methyl-1-[6-(4-piperazin-1-yl-phenylamino)-pyrimidin-4-yl]-urea A suspension of 1-{6-[4-(4-benzyl-piperazin-1-yl)-phenylamino]-pyrimidin-4-yl}-3-(2,6-dichloro-3,5-dimethoxy-6-methyl-phenyl)-1-methyl-urea (100 mg, 0.161 mmol) (Example 13), palladium on carbon (30 mg), MeOH (6 mL), and HCl (37%, 16 μL) is stirred for 5 days at RT, under a hydrogen atmosphere. The reaction mixture is filtered and concentrated. Purification of the residue by silica gel column chromatography (DCM/2N $NH_3$ in MeOH, 95:5) affords the title compound as a beige solid: ESI-MS: 532.0/534.0 $[MH]^+$; $t_R$=3.39 min (purity: 100%, system 1).

Example 15

3-(2-Chloro-3,5-dimethoxy-6-methyl-phenyl)-1-[6-(3-dimethylaminomethyl-phenylamino)-pyrimidin-4-yl]-1-methyl-urea The title compound is prepared in analogy to the procedure described in Example 2: ESI-MS: 485.0/487.0 [MH]$^+$; $t_R$=3.69 min (purity: 100%, system 1).

Example 16

3-(2-Chloro-3,5-dimethoxy-6-methyl-phenyl)-1-{6-[3-(4-ethyl-piperazin-1-yl)phenylamino]-pyrimidin-4-yl}-1-methyl-urea The title compound is prepared in analogy to the procedure described in Example 2: ESI-MS: 540.0/542.0 [MH]$^+$; $t_R$=3.74 min (purity: 100%, system 1).

Example 17

3-(2-Chloro-3,5-dimethoxy-6-methyl-phenyl)-1-methyl-1-{6-[4-(2s-pyrrolidin-1-ylethoxy)-phenylamino]-pyrimidin-4-yl}-1-methyl-urea The title compound is prepared in analogy to the procedure described in Example 2: ESI-MS: 541.0/543.0 [MH]$^+$; $t_R$=3.66 min (purity: 100%, system 1).

Step 17.1: N-Methyl-N'-[4-(2-pyrrolidin-1-yl-ethoxy)-phenyl]-pyrimidine-4,6-diamine The title compound is prepared in analogy to the procedure described in Step 2.1: ESI-MS: 314.1 [MH]$^+$; $t_R$=1.15 min (system 1); TLC: $R_f$=0.15 (DCM/MeOH+1% NH$_3$$^{aq}$, 9:1).

Step 17.2: 4-(2-Pyrrolidin-1-yl-ethoxy)-phenylamine

The title compound is prepared in analogy to the procedure described in Step 1.2: ESI-MS: 207.1 [MH]$^+$; TLC: $R_f$=0.22 (DCM/MeOH, 1:1).

Example 18

3-(2-Chloro-3,5-dimethoxy-6-methyl-phenyl)-1-methyl-1-{6-[3-fluoro-4-(2-pyrrolidin-1-yl-ethoxy)-phenylamino]-pyrimidin-4-yl}-1-methyl-urea The title compound is prepared in analogy to the procedure described in Example 2: ESI-MS. 578.9/580.9 [MH]$^+$; $t_R$=3.96 min (purity: 100%, system 1); TLC: $R_f$=0.38 (DCM/MeOH+1% NH$_3$$^{aq}$, 92:8).

Step 18.1: N-[3-Fluoro-4-(2-pyrrolidin-1-yl-ethoxy)-phenyl]-N'-methyl-pyrimidine-4,6-diamine The title compound is prepared in analogy to the procedure described in Step 1.1; ESI-MS: 332.2 [MH]$^+$; $t_R$=1.30 min (system 1); TLC: $R_f$=0.37 (DCM/MeOH+1% NH$_3$$^{aq}$, 99:1).

Step 18.2: 3-Fluoro-4-(2-pyrrolidin-1-yl-ethoxy)-phenylamine

A suspension of 1-[2-(2-fluoro-4-nitro-phenoxy)-ethyl]-pyrrolidine (1.25 g, 4.92 mmol) and 10% palladium on carbon (0.2 g) in EtOH (20 mL) is stirred for 1 h at RT, under a hydrogen atmosphere. The reaction mixture is filtered through a pad of celite and concentrated to afford the title compound as a brown oil: ESI-MS: 225.1 [MH]$^+$; $t_R$=0.80 min (system 1).

Step 18.3: 1-[2-(2-Fluoro-4-nitro-phenoxy)-ethyl]-pyrrolidine 1-(2-Chloro-ethyl)-pyrrolidine hydrochloride (1.2 g, 7.0 mmol, 1.1 equiv) is added to a suspension of 2-fluoro-4-nitrophenol (1 g, 6.4 mmol) and cesium carbonate (5.2 g, 15.9 mmol, 2.5 equiv) in DMF (20 mL). The resulting mixture is heated to 80° C. and stirred for 18 h. Additional 1-(2-chloroethyl)-pyrrolidine hydrochloride (1 g) is added and the mixture is stirred for 3 h at 80° C. The reaction mixture is cooled to RT, diluted with EtOAc and H$_2$O. The layers are separated and the aqueous layer is extracted with EtOAc. The organic phase is washed with H$_2$O, dried (Na$_2$SO$_4$), filtered and concentrated. The residue is purified by silica gel column chromatography (DCM/MeOH+1% NH$_3$$^{aq}$, 95:5) to provide the title compound as a yellow solid. ESI-MS: 255.1 [MH]$^+$; $t_R$=2.57 min (system 1); TLC: $R_f$=0.55 (DCM/MeOH+1% NH$_3$$^{aq}$, 95:5).

Example 19

3-(2,6-Dichloro-3,5-dimethoxy-phenyl)-1-{6-[4-(1-ethyl-piperidin-4-yl)-phenylamino]-pyrimidin-4-yl}-1-methyl-urea The title compound is prepared in analogy to the procedure described in Example 2: ESI-MS: 558.9/560.9 [MH]$^+$; $t_R$=3.85 min (purity: 100%, system 1); TLC: $R_f$=0.14 (DCM/MeOH+1% NH$_3$$^{aq}$, 95:5).

Step 19.1: N-[4-(1-Ethyl-piperidin-4-yl)-phenyl-N'-methyl-pyrimidine-4,6-diamine The title compound is prepared in analogy to the procedure described in Step 1.1: ESI-MS: 312.2 [MH]$^+$; $t_R$=1.3 min (system 1); TLC: $R_f$=0.27 (DCM/MeOH+1% NH$_3$$^{aq}$, 92:8).

Step 19.2: 4-(1-Ethyl-Piperidin-4-yl)-phenylamine

A suspension of 1-ethyl-4-(4-nitro-phenyl)-piperidine (0.8 g, 4.92 mmol) and 10% palladium on carbon (0.1 g) in EtOH (10 mL) is stirred for 3 h at RT, under a hydrogen atmosphere. The reaction mixture is filtered through a pad of celite and concentrated. The residue is purified by silica gel column chromatography (DCM/MeOH+1% NH$_3$$^{aq}$, 95:5) to provide the title compound. ESI-MS: 205.1 [MH]$^+$; TLC: $R_f$=0.29 (DCM/MeOH+1% NH$_3$$^{aq}$, 95:5).

Step 19.3: 1-Ethyl-4-(4-nitro-phenyl)-piperidine

Sodium triacetoxyborohydride (3.1 g, 14.6 mmol, 3 equiv) is added to a cold (5° C.) solution of 4-(4-nitro-phenyl)-piperidine (1 g, 4.9 mmol) and acetaldehyde (0.82 mL, 14.6 mmol, 3 equiv) in DCM (20 mL). The reaction mixture is stirred for 1 h at 5° C. and then diluted with DCM and a saturated aqueous solution of NaHCO$_3$. The layers are separated and the aqueous layer is extracted with DCM. The organic phase is washed with brine, dried (Na$_2$SO$_4$), filtered and concentrated. The residue is purified by silica gel column chromatography (DCM/MeOH+1% NH$_3$$^{aq}$, 98:2) to provide the title compound as a yellow oil. ESI-MS: 235.1 [MH]$^+$; $t_R$=2.64 min (purity: 85%, system 1); TLC: $R_f$=0.14 (DCM/MeOH+1% NH$_3$$^{aq}$, 98:2).

Step 19.4: 4-(4-Nitro-phenyl)-piperidine

A solution of conc. $H_2SO_4$ (2.65 mL) in AcOH (40 mL) and a solution of conc. $HNO_3$ (2.1 mL) in AcOH (20 mL) are added sequentially and dropwise to a solution of 4-phenylpiperidine in AcOH (40 mL), maintaining the temperature below 20° C. Then, conc. $H_2SO_4$ (40 mL) is added (no cooling applied; internal temperature reaches 60° C.). The reaction mixture is allowed to cool to RT, poured onto ice/water (100 g), neutralized by addition of solid $NaHCO_3$ (150 g), and extracted with DCM. The organic phase is washed with brine, dried ($Na_2SO_4$), filtered and concentrated. The residue is purified by trituration in $Et_2O$ to afford the title compound as a yellow solid. ESI-MS: 207.1 $[MH]^+$; $t_R$=2.42 min (system 1).

Example 20

3-(2,6-Dichloro-3,5-dimethoxy-phenyl)-1-ethyl-1-{6-[4-(4-ethyl-piperazin-1-yl)phenylamino]-pyrimidin-4-yl}-urea The title compound is prepared in analogy to the procedure described in Example 2: ESI-MS: 573.9/575.9 $[MH]^+$; $t_R$=3.69 min (purity: 100%, system 1).

Step 20.1: N-Ethyl-N'-[4-(4-ethyl-piperazin-1-yl)-phenyl]-pyrimidine-46-diamine The title compound is prepared in analogy to the procedure described in Step 1.1: ESI-MS: 327.2 $[MH]^+$; $t_R$=1.5 min (system 1).

Example 21

3-(2,6-Dichloro-3,5-dimethoxy-phenyl)-1-{6-[2-fluoro-4-(2-pyrrolidin-1-ylethoxy)-phenylamino]-pyrimidin-4-yl}-1-methyl-urea The title compound is prepared in analogy to the procedure described in Example 2: ESI-MS: 578.9/580.9 $[MH]^+$; $t_R$=3.79 min (purity: 100%, system 1).

Step 21.1: N-[2-Fluoro-4-(2-pyrrolidin-1-yl-ethoxy)-phenyl]-N'-methyl-pyrimidine-4,6-diamine The title compound is prepared in analogy to the procedure described in Step 2.1: ESI-MS: 332.2 $[MH]^+$.

Step 21.2: 2-Fluoro-4-(2-pyrrolidin-1-yl-ethoxy)-phenylamine

A suspension of 1-[2-(3-fluoro-4-nitro-phenoxy)-ethyl]-pyrrolidine (1.96 g, 7.7 mmol) and 10% palladium on carbon (0.2 g) in MeOH (40 mL) is stirred for 0.5 h at RT, under a hydrogen atmosphere. The reaction mixture is filtered through a pad of celite and concentrated to provide the title compound. ESI-MS: 225.1 [MH]; $t_R$=0.95 min (system 1).

Step 21.3: 1-[2-(3-Fluoro-4-nitro-phenoxy)-ethyl]-pyrrolidine 1-(2-Chloro-ethyl)-pyrrolidine hydrochloride (2.6 g, 15.4 mmol, 1.3 equiv) is added to a mixture of 2-fluoro-4-nitro-phenol (1.84 g, 11.7 mmol) and cesium carbonate (9.1 g, 27.9 mmol, 2.5 equiv) in DMF (40 mL). The resulting mixture is heated to 80° C. and stirred for 3 h. The reaction mixture is cooled to RT, then diluted with DCM and $H_2O$. The layers are separated and the aqueous layer is extracted with DCM. The organic phase is washed with brine, dried ($Na_2SO_4$), filtered and concentrated. The residue is purified by silica gel column chromatography (DCM/MeOH+1% $NH_3^{aq}$, 97:3) to provide 1.96 g of the title compound as a dark yellow solid. ESI-MS: 255.1 $[MH]^+$; $t_R$=2.55 min (purity: 93%, system 1); TLC: $R_f$=0.40 (DCM/MeOH+1% $NH_3^{aq}$, 93:7).

Example 22

3-(2,6-Dichloro-3,5-dimethoxy-phenyl)-1-{6-[4-(4-ethyl-piperazin-1-yl)-2-methoxy-phenylamino]-pyrimidin-4-yl}-1-methyl-urea The title compound is prepared in analogy to the procedure described in Example 2 API-MS: 589.9/591.8 $[MH]^+$; $t_R$=3.59 min (system 1); TLC: $R_f$=0.13 (DCM/MeOH+0.5% $NH_3^{aq}$, 95:5).

Step 22.1: N-[4-(4-Ethyl-piperazin-1-yl)-2-methoxy-phenyl]-N'-methyl-pyrimidine-4,6-diamine The title compound is prepared in analogy to the procedure described in Step 1.1: ESI-MS: 343.2 $[MH]^+$; $t_R$=1.30 min (system 1).

Step 22.2: 4-(4-Ethyl-piperazin-1-yl)-2-methoxy-phenylamine

A suspension of 1-ethyl-4-(3-methoxy-4-nitro-phenyl)-piperazine (4 g, 15.1 mmol) and Raney Nickel (1 g) in MeOH (80 mL) is stirred for 10.5 h at RT, under a hydrogen atmosphere. The reaction mixture is filtered through a pad of celite and concentrated to afford the title compound as a brown oil: ESI-MS: 236.2 $[MH]^+$; $t_R$=0.95 min (system 1).

Step 22.3: 1-Ethyl-4-(3-methoxy-4-nitro-phenyl)-piperazine

The title compound is prepared in analogy to the procedure described in Step 248.3: ESI-MS: 266.1 $[MH]^+$.

Example 23

3-(2,6-Dichloro-3,5-dimethoxy-phenyl)-1-{6-[4-(4-ethyl-piperazine-1-carbonyl)-phenylamino]-pyrimidin-4-yl}-1-methyl-urea The title compound is prepared in analogy to the procedure described in Example 233: API-MS: 587.8/589.8 $[MH]^4$: $t_R$=3.58 min (purity: 94.8%, system 1); TLC: $R_f$=0.47 (DCM/2N $NH_3$ in MeOH, 9:1).

Step 23.1: (4-Ethyl-piperazin-1-yl)-[4-(6-methylamino-pyrimidin-4-ylamino)-phenyl]-methanone Propylphosphonic anhydride (50% in DMF, 2.72 mL, 4.7 mmol, 2 equiv) is added to a solution of 4-(6-methylamino-pyrimidin-4-ylamino)-benzoic acid (0.570 g, 2.33 mmol), N-ethyl-piperazine (0.33 mL, 2.57 mmol, 1.1 equiv), DMAP (7 mg), and $Et_3N$ (3.3 mL, 23.3 mmol, 10 equiv) in DMF (25 mL), at RT and under an argon atmosphere. The reaction mixture is stirred at RT for 1 h, diluted with EtOAc and washed with $H_2O$. The aqueous layer is extracted with EtOAc. The combined organic phase is washed with brine, dried ($Na_2SO_4$), filtered and concentrated. The residue is purified by silica gel column chromatography (DCM→DCM/2 N NH$_3$ in MeOH, 86:14) to provide the title compound as a yellow foam: ES-MS: 341.2 [MH]$^+$; t$_R$=1.00 min (system 1); R$_f$=0.33 (CH$_2$Cl$_2$/2 N NH$_3$ in MeOH, 9:1).

Step 23.2:
4-(6-Methylamino-pyrimidin-4-ylamino)-benzoic acid

The title compound is prepared in analogy to the procedure described in Step 2.1: ESI-MS: 245.0 [MH]$^+$; t$_R$=1.58 min (system 1).

Example 24

3-(2,6-Dichloro-3,5-dimethoxy-phenyl)-1-{6-[4-(4-ethyl-piperazin-1-yl)-3-fluoro-phenylamino]-pyrimidin-4-yl}-1-methyl-urea The title compound is prepared in analogy to the procedure described in Example 2: API-MS: 577.9/579.9 [MH]$^+$; t$_R$=3.87 min (purity: 90%, system 1); TLC: R$_f$=0.20 (DCM/MeOH+1% NH$_3^{aq}$, 95:5).

Step 24.1: N-[4-(4-Ethyl-piperazin-1-yl)-3-fluoro-phenyl]-N'-methyl-pyrimidine-46-diamine The title compound is prepared in analogy to the procedure described in Step 2.1, but stirring the reaction mixture for 15 min at 160° C. in a microwave apparatus. The crude product is purified by trituration in EtOAc to afford the title compound: ESI-MS: 331.2 [MH]$^+$.

Step 24.2:
4-(4-Ethyl-piperazin-1-yl)-3-fluoro-phenylamine

A suspension of 1-ethyl-4-(2-fluoro-4-nitro-phenyl)-piperazine (1.24 g, 15.1 mmol) and Raney Nickel (13 mg) in MeOH (6 mL) is stirred for 17 h at RT, under a hydrogen atmosphere. The reaction mixture is filtered through a pad of celite and concentrated to afford the title compound as a purple oil: ESI-MS: 224.1 [MH]$^+$; t$_R$=0.90 min (system 1).

Step 24.3:
1-Ethyl-4-(2-fluoro-4-nitro-phenyl)-piperazine

N-Ethylpiperazine (0.96 mL, 7.6 mmol, 1.2 equiv) is added to a mixture of 3,4-difluoronitrobenzene (0.7 mL, 6.32 mmol) and potassium carbonate (1.74 g, 12.6 mmol, 2 equiv) in DMF (10 mL). The reaction mixture is stirred at 90° C. for 17 h, allowed to cool to RT, diluted with H$_2$O and extracted with DCM. The organic phase is washed with brine, dried (Na$_2$SO$_4$), filtered and concentrated. The residue is purified by silica gel column chromatography (DCM/MeOH+1% NH$_3^{aq}$, 97:3) to provide the title compound as a yellow solid: ES-MS: 254.1 [MH]$^+$; t$_R$=2.65 min (system 1); R$_f$=0.30 (DCM/MeOH+1% NH$_3^{aq}$, 93:7).

Example 25

3-(2,4-Dichloro-5-methoxy-3-trifluoromethyl-phenyl)-1-{6-[4-(4-ethyl-piperazin-1-yl)-phenylamino]-pyrimidin-4-yl}-1-methyl-urea Phosgene (20% in toluene, 0.54 mL, 1.0 mmol, 2.0 equiv) is added to a solution of 2,4-dichloro-5-methoxy-3-trifluoromethylaniline (156 mg, 0.60 mmol, 1.2 equiv) in dioxane (2 mL), under a nitrogen atmosphere. The mixture is heated to reflux, stirred for 75 min, allowed to cool to RT, and concentrated in vacuo. The resulting solid 2,4-dichloro-5-methoxy-3-trifluoromethyl-phenylisocyanate is added portion-wise to a boiling solution of N-[4-(4-ethyl-piperazin-1-yl)-phenyl]-N'-methyl-pyrimidine-4,6-diamine (156 mg, 0.50 mmol; preparation see Step 25.5) in 6 ml of toluene under a nitrogen atmosphere. The reaction mixture is stirred at 110° C. for 3.3 h, allowed to cool to RT, and diluted with DCM and a saturated aqueous solution of NaHCO$_3$. The aqueous layer is separated off and extracted twice with DCM. The organic phase is washed with brine, dried (Na$_2$SO$_4$), filtered and concentrated. Trituration of the resulting solid with 2 portions of MeOH yields the title compound: ESI-MS: 598/600 [MH]$^+$; t$_R$=5.1 min (purity: 97%, system 1).

Step 25.1:
2,4-Dichloro-5-methoxy-3-trifluoromethylaniline

A 2 M solution of KOH in water (1.87 mL) is added to a solution of N-(2,4-dichloro-5-methoxy-3-trifluoromethyl-phenyl)-acetamide (104 mg, 0.344 mmol) in EtOH (3 mL). After stirring for 3.5 h at 80° C. followed by cooling to RT, the solvent is evaporated and the residue is taken up in EtOAc and a saturated aqueous solution of NaHCO$_3$. The separated aqueous layer is extracted twice with EtOAc. The organic phases are washed with brine, dried (Na$_2$SO$_4$), filtered and concentrated, providing the title compound: ESI-MS: 258/260 [M-H]$^-$; t$_R$=4.8 min (system 1); TLC: R$_f$=0.54 (EtOAc).

Step 25.2: N-(2,4-Dichloro-5-methoxy-3-trifluoromethyl-phenyl)-acetamide

A solution of N-(5-methoxy-3-trifluoromethyl-phenyl)-acetamide (233 mg, 1.0 mmol) under a nitrogen atmosphere is cooled in a ice-bath (precipitation). Then 1.93 mL of a 1 M solution of SO$_2$Cl$_2$ in DCM are added. After 2 h, another 1.93 mL of the SO$_2$Cl$_2$ solution are added and stirring is continued for totally 4 h at 0° C. The suspension is diluted with DCM and a saturated aqueous solution of NaHCO$_3$. The separated inorganic phase is extracted twice with DCM. The organic phases are washed with water and brine, dried (Na$_2$SO$_4$), filtered and concentrated. Column chromatography (hexane/EtOAc, 7:3) provides the title compound: mp: 143-144° C.; API-MS: 300/302 [M-H]$^-$; TLC: R$_f$=0.23 (Hex/EtOAc, 1:1); $^1$H-NMR (DMSO-d$_6$) δ 2.13 (s, H$_3$C), 3.88 (s, H$_3$C), 7.84 (s, H$_{phenyl}$), 9.81 (s, HN).

Step 25.3:
N-(5-Methoxy-3-trifluoromethyl-phenyl)-acetamide

Acetic anhydride (1.22 ml, 12.8 mmol) is added during 10 min to a solution of 5-methoxy-3-trifluoromethyl-aniline (2.29 g, 12.0 mmol) in toluene (10 ml) at a temperature of 25-33° C. After 90 min at RT, hexane (10 ml) is added und the suspension is stirred for 20 min. Filtration, washing with toluene/hexane 2:1 and hexane gives the title compound: mp: 123-124° C.; API-MS: 234 [MH]$^+$; TLC: R$_f$=0.27 (Hex/EtOAc, 1:1).

Step 25.4: 5-Methoxy-3-trifluoromethyl-aniline

Hydrogenation of a solution of 3-methoxy-5-nitrobenzotrifluoride (6.19 g, 28 mmol) in MeOH (140 ml) in the presence of Pd—C (0.62 g, 10%), removal of the catalyst by filtration and concentration in vacuo of the resulting filtrate gives the title compound: API-MS: 190 [M-H]⁻; TLC: $R_f$=0.7 (EtOAc).

Step 25.5: N-[4-(4-ethyl-piperazin-1-yl)-phenyl]-N'-methyl-pyrimidine-4,6-diamine A mixture of 4-(4-ethylpiperazin-1-yl)-aniline (1 g, 4.88 mmol) (prepared in analogy to Example 238, Step 238.1), (6-chloro-pyrimidin-4-yl)-methyl-amine (1.81 g, 12.68 mmol, 1.3 eq.) and 4N HCl in dioxane (15 ml) is heated in a sealed tube to 150° C. for 5 h. The reaction mixture is concentrated, diluted with DCM and a saturated aqueous solution of sodium bicarbonate. The aqueous layer is separated and extracted with DCM. The organic phase is washed with brine, dried (sodium sulfate), filtered and concentrated. Purification of the residue by silica gel column chromatography (DCM/MeOH, 93:7) followed by trituration in diethyl ether affords the title compound as a white solid: ESI-MS: 313.2 [MH]⁺; $t_R$=1.10 min (system 1); TLC: $R_f$=0.21 (DCM/MeOH, 93:7).

Example 26

3-(5-Methoxy-3-trifluoromethyl-phenyl)-1-{6-[4-(4-ethyl-piperazin-1-yl)phenylamino]-pyrimidin-4-yl}-1-methyl-urea Phosgene (20% in toluene, 1.62 mL, 3.0 mmol, 2.0 equiv) is added to a solution of 5-methoxy-3-trifluoromethylaniline (344 mg, 1.8 mmol, 1.2 equiv) in dioxane (6 mL) under a nitrogen atmosphere. The mixture is heated to reflux, stirred for 80 min, allowed to cool to RT, and concentrated in vacuo. During 45 min, a concentrated solution of the resulting oily 5-methoxy-3-trifluoromethyl-phenylisocyanate in toluene is added portion-wise to a boiling solution of N-[4-(4-ethyl-piperazin-1-yl)-phenyl]-N'-methyl-pyrimidine-4,6-diamine (468 mg, 1.50 mmol; Step 242.1) in 18 ml of toluene under a nitrogen atmosphere. The reaction mixture is stirred at 110° C. for 4 h, allowed to cool to RT, and diluted with DCM and a saturated aqueous solution of NaHCO₃. The aqueous layer is separated and extracted twice with DCM. The organic phases are washed with brine, dried (Na₂SO₄), filtered and concentrated. Column chromatography (DCM/MeOH, 49:1→24:1) provides the title compound: API-MS: 530/532 [MH]⁺; TLC: $R_f$=0.4 (DCM/MeOH, 9:1); $t_R$=4.3 min (purity: 100%, system 1).

Example 27

3-(5-Methoxy-3-trifluoromethyl-phenyl)-1-{6-[3-chloro-4-(4-ethyl-piperazin-1-yl)phenylamino]-pyrimidin-4-yl}-1-methyl-urea Portions of 0.4 mL of a 1 M solution of SO₂Cl₂ in DCM are added repeatedly over a period of 27 h to an ice-cooled suspension of 3-(5-methoxy-3-trifluoromethyl-phenyl)-1-{6-[4-(4-ethylpiperazin-1-yl)-phenylamino]-pyrimidin-4-yl}-1-methyl-urea (105 mg, 0.20 mmol) (Example 26) in acetonitrile (6 mL). The reaction is followed by HPLC analysis. The reaction mixture (still containing starting material) is diluted with DCM and a saturated aqueous solution of NaHCO₃. The aqueous layer is separated and extracted twice with DCM. The organic phases are washed with brine, dried (Na₂SO₄), filtered and concentrated. Reversed phase MPLC (H₂O/CH₃CN+0.1% TFA) yields, after neutralization of the product containing fractions with NaHCO₃, partial concentration and extraction with DCM, the title compound: API-MS: 564/566 [MH]⁺; TLC: $R_f$=0.28 (DCM/MeOH+1% NH₃$^{aq}$, 95:5); ¹H-NMR (DMXO-d₆) δ 1.02 (t, H₃C), 2.37 (q, H₂C), 2.51 (m, 4H), 2.92 (m, 4H), 3.33 (s, H₃C), 3.82 (s, H₃C), 6.48 (s, 1H), 6.90 (s, 1H), 7.12 (d, 1H), 7.43 (m, 2H), 7.59 (s, 1H), 7.82 (s, 1H), 8.55 (s, 1H), 9.66 (s, HN), 12.33 (s, HN).

Example 28

1-{6-[2-Chloro-4-(4-ethyl-piperazin-1-yl)-phenylamino]-pyrimidin-4-yl}-3-(2,6-dichloro-3,5-dimethoxy-phenyl)-1-methyl-urea The title compound is prepared in analogy to the procedure described in Example 2 (1 h 20 min stirring at reflux): ESI-MS: 593.8/595.8 [MH]⁺; $t_R$=3.80 min (purity: 95%, system 1); TLC: $R_f$=0.45 (DCM/MeOH+1% NH₃$^{aq}$, 95:5).

Step 28.1: N-[2-Chloro-4-(4-ethyl-piperazin-1-yl)-phenyl]-N'-methyl-pyrimidine-4,6-diamine The title compound is prepared in analogy to the procedure described in Step 1.1: ESI-MS: 347.1/349.1 [MH]⁺; TLC: $R_f$=0.15 (DCM/MeOH+1% NH₃$^{aq}$, 95:5).

Step 28.2: 2-Chloro-4-(4-ethyl-piperazin-1-yl)-phenylamine

A suspension of 1-(3-chloro-4-nitro-phenyl)-4-ethyl-piperazine (1 g, 3.7 mmol) and Raney Nickel (0.1 g) in MeOH (20 mL) is stirred for 8 h at RT, under a hydrogen atmosphere. The reaction mixture is filtered through a pad of celite and concentrated. The residue is purified by silica gel column chromatography (DCM/MeOH+1% NH₃$^{aq}$, 95:5) to afford the title compound as an off-white solid: ESI-MS: 240.1/242.1 [MH]⁺; $t_R$=0.90 min (system 1), TLC: $R_f$=0.46 (DCM/MeOH+1% NH₃$^{aq}$, 95:5).

Step 28.3: 1-(3-Chloro-4-nitro-phenyl)-4-ethyl-piperazine

N-Ethylpiperazine (4.3 mL, 34.3 mmol, 1.2 equiv) is added to a mixture of 2-chloro-4-fluoronitrobenzene (5 g, 28.6 mmol) and potassium carbonate (7.9 g, 57.1 mmol, 2 equiv) in DMF (50 mL). The reaction mixture is stirred at 100° C. for 6 h, allowed to cool to RT, diluted with H₂O and extracted with EtOAc. The organic phase is washed with brine, dried (Na₂SO₄), filtered and concentrated. The residue is purified by trituration in diethyl ether to provide 5.6 g of the title compound as a yellow solid: ES-MS: 270.0 [MH]⁺; $t_R$=2.90 min (system 1).

Example 29

3-(2,6-Dichloro-3,5-dimethoxy-phenyl)-1-{6-[4-(4-ethyl-piperazin-1-yl)-2-fluoro-phenylamino]-pyrimidin-4-yl}-1-methyl-urea The title compound is prepared in analogy to the procedure described in Example 2 (1 h stirring at reflux, and EtOAc used instead of DCM to extract the product): ESI-MS: 577.9/579.9 [MH]⁺; $t_R$=4.00 min (purity: >95%, system 1); TLC: $R_f$=0.35 (DCM/MeOH+1% NH₃$^{aq}$, 97:3).

Step 29.1: N-[4-(4-Ethyl-piperazin-1-yl)-2-fluoro-phenyl]-N'-methyl-pyrimidine-4-O-diamine The title compound is prepared in analogy to the procedure described in Step 2.1, but stirring the reaction mixture for 1 h at 160° C. in a microwave apparatus and using EtOAc instead of DCM to extract the product. Title compound: ESI-MS: 331.1 [MH]$^+$; TLC: R$_f$=0.10 (DCM/MeOH+1% NH$_3^{aq}$, 95:5).

Step 29.2:
4-(4-Ethyl-piperazin-1-yl)-2-fluoro-phenylamine

A suspension of 1-ethyl-4-(3-fluoro-4-nitro-phenyl)-piperazine (7 g, 27.7 mmol) and Pd (10%) on carbon (0.35 g) in MeOH (140 mL) is stirred for 3 h at RT, under a hydrogen atmosphere. The reaction mixture is filtered through a pad of celite and concentrated. The residue is purified by silica gel column chromatography (DCM/MeOH+1% NH$_2^{aq}$, 95:5) to afford the title compound as a white solid: ESI-MS: 224.1 [MH]$^+$; TLC: R$_f$=0.54 (DCM/MeOH+1% NH$_3^{aq}$, 95:5).

Step 29.3:
1-Ethyl-4-(3-fluoro-4-nitro-phenyl)-piperazine

N-Ethylpiperazine (4.8 mL, 37.7 mmol, 1.2 equiv) is added to a mixture of 2,4-difluoronitrobenzene (5 g, 31.4 mmol) and potassium carbonate (8.7 g, 62.9 mmol, 2 equiv) in DMF (50 mL). The reaction mixture is stirred at 100° C. for 6 h, allowed to cool to RT, diluted with H$_2$O and extracted with EtOAc. The organic phase is washed with brine, dried (Na$_2$SO$_4$), filtered and concentrated. The residue is purified by silica gel column chromatography (DCM/MeOH+1% NH$_3^{aq}$, 95:5) to provide the title compound as a yellow oil: ES-MS: 254.1 [MH]$^+$; TLC: R$_f$=0.67 (DCM/MeOH+1% NH$_3^{aq}$, 95:5).

Example 30

3-(2,6-Dichloro-3,5-dimethoxy-phenyl)-1-{6-[6-(4-isopropyl-piperazin-1-yl)pyridin-3-ylamino]-pyrimidin-4-yl}-1-methyl-urea The title compound is prepared in analogy to the procedure described in Example 1 (2 equiv of phosgene for the isocyanate formation, 16 h stirring at 70° C. in the subsequent step, and EtOAc used instead of DCM to extract the product): ESI-MS: 574.8/576.8 [MH]$^+$; t$_R$=3.32 min (system 1); TLC: R$_f$=0.10 (DCM/MeOH/NH$_3^{aq}$, 94:5:1).

Step 30.1: N-[6-(4-Isopropyl-piperazin-1-yl)-pyridin-3-yl]-N'-methyl-pyrimidine-4,6-diamine The title compound is prepared in analogy to the procedure described in Step 1.1. Title compound: ESI-MS: 328.2 [MH]$^+$.

Step 30.2:
6-(4-isopropyl-piperazin-1-yl)-pyridin-3-ylamine

A mixture of iron powder (1.4 g, 25.3 mmol, 4 equiv), 1-isopropyl-4-(5-nitro-pyridin-2-yl)piperazine (1.58 g, 6.32 mmol), EtOH (20 mL), H$_2$O (5 mL), and AcOH (2.5 mL) is stirred for 2 h at 90° C., allowed to cool to RT, basified by addition of aqueous ammonia, filtered through a pad of celite and partially concentrated to remove EtOH. The aqueous residue is saturated with sodium chloride and extracted with EtOAc and DCM. The combined organic phase is washed with brine, dried (Na$_2$SO$_4$), filtered and concentrated. The residue is purified by silica gel column chromatography (DCM/MeOH/NH$_3^{aq}$, 91:8:1) to afford the title compound as a purple solid: ESI-MS: 221.1 [MH]$^+$; TLC: R$_f$=0.20 (DCM/MeOH/NH$_3^{aq}$, 91:8:1).

Step 30.3: 1-Isopropyl-4-(5-nitro-pyridin-2-yl)-piperazine (NVP-BKT293)

N-Isopropylpiperazine (1.8 mL, 12.7 mmol, 2 equiv) is added to a cold (5° C.) mixture of 2-chloro-5-nitropyridine (1 g, 6.3 mmol) in DCM (5 mL). The reaction mixture is allowed to warm to RT, stirred for 16 h, diluted with DCM/H$_2$O and extracted with DCM. The organic phase is washed with brine, dried (Na$_2$SO$_4$), filtered and concentrated to provide the title compound as a yellow solid: ES-MS: 251.2 [MH]$^+$; t$_R$=2.20 min (system 1).

Example 31

3-(2,6-Dichloro-3,5-dimethoxy-phenyl)-1-{6-[6-(4-ethyl-piperazin-1-yl)-pyridin-3-ylamino]-pyrimidin-4-yl}-1-methyl-urea The title compound is prepared in analogy to the procedure described in Example 1 (2 equiv of phosgene for the isocyanate formation, 4 h stirring at reflux in the subsequent step, and EtOAc used instead of DCM to extract the product): ESI-MS: 560.8/562.8 [MH]$^+$; t$_R$=3.20 min (system 1); TLC: R$_f$=0.35 (DCM/MeOH/NH$_3^{aq}$, 94:5:1).

Step 31.1: N-[6-(4-Ethyl-piperazin-1-yl)-pyridin-3-yl]-N'-methyl-pyrimidine-4,6-diamine The title compound is prepared in analogy to the procedure described in Step 1.1. Title compound: ESI-MS: 314.2 [MH]$^+$; TLC: R$_f$=0.20 (DCM/MeOH/NH$_3^{aq}$, 91:8:1).

Step 31.2:
6-(4-Ethyl-piperazin-1-yl)-pyridin-3-ylamine

A suspension of 1-ethyl-4-(5-nitro-pyridin-2-yl)-piperazine (1.4 g) and Raney-Nickel (140 mg) in MeOH (30 mL) is stirred for 10 h at RT, under a hydrogen atmosphere. The reaction mixture is filtered through a pad of celite and concentrated. The residue is purified by silica gel column chromatography (DCM/MeOH/NH$_3^{aq}$, 94:5:1) to afford the title compound as a purple oil: ESI-MS: 207.1 [MH]$^+$; TLC: R$_f$=0.26 (DCM/MeOH/NH$_3^{aq}$, 94:5:1).

Step 31.3: 1-Ethyl-4-(5-nitro-pyridin-2-yl)-piperazine

The title compound is prepared in analogy to the procedure described in Step 30.3 but using N-ethylpiperazine. The title compound: ES-MS: 237.1 [MH]$^+$; TLC: R$_f$=0.25 (DCM/MeOH/NH$_3^{aq}$, 96:3:1).

Example 32

Soft Capsules 5000 soft gelatin capsules, each comprising as active ingredient 0.05 g of any one of the compounds of formula IA mentioned in any one of the preceding Examples 1 to 29 or are prepared as follows:

| Composition | |
|---|---|
| Active ingredient | 250 g |
| Lauroglycol | 2 liters |

Preparation process: The pulverized active ingredient is suspended in Laurogiykol* (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 33

Tablets Comprising Compounds of the Formula IA

Tablets, comprising, as active ingredient, 100 mg of any one of the compounds of formula IA in any one of the preceding Examples 1 to 29 are prepared with the following composition, following standard procedures:

| Composition | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, stamp diameter 10 mm).

Avicel® is microcrystalline cellulose (FMC, Philadelphia, USA). PVPPXL is polyvinylpolypyrrolidone, cross-linked (BASF, Germany). Aerosil® is silicon dioxide (Degussa, Germany).

The invention claimed is:

1. A compound 3-(2,6-Dichloro-3,5-dimethoxy-phenyl)-1-methyl-1-[6-(4-piperazin-1-yl-phenylamino)-pyrimidin-4-yl]-urea of the formula

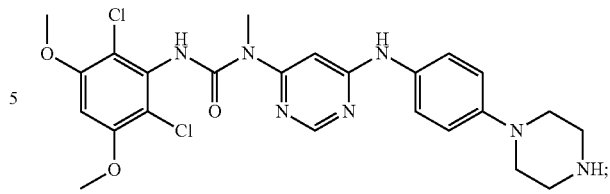

or a salt thereof.

2. A compound 3-(2,6-Dichloro-3,5-dimethoxy-phenyl)-1-methyl-1-[6-(4-piperazin-1-yl-phenylamino)-pyrimidin-4-yl]-urea of the formula

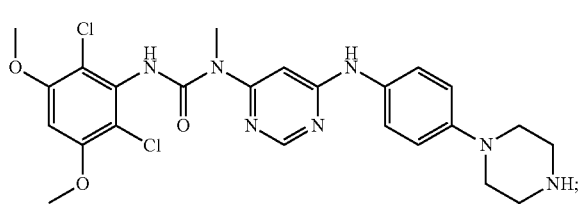

or a pharmaceutically acceptable salt thereof.

3. A pharmaceutical composition comprising a compound according to claim 2 or a pharmaceutically acceptable salt thereof and a pharmaceutically acceptable carrier.

4. A compound 3-(2,6-Dichloro-3,5-dimethoxy-phenyl)-1-methyl-1-[6-(4-piperazin-1-yl-phenylamino)-pyrimidin-4-yl]-urea of the formula

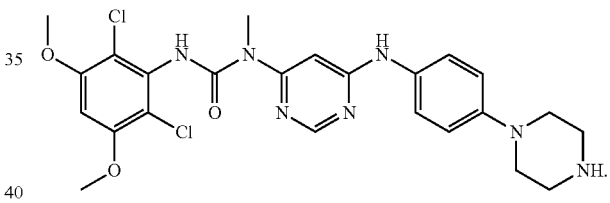

5. A pharmaceutical composition comprising a compound according to claim 4 and a pharmaceutically acceptable carrier.

* * * * *